(12) United States Patent
Katz et al.

(10) Patent No.: US 12,073,935 B2
(45) Date of Patent: Aug. 27, 2024

(54) SYSTEMS AND METHODS FOR DIET QUALITY PHOTO NAVIGATION UTILIZING DIETARY FINGERPRINTS FOR DIET ASSESSMENT

(71) Applicant: Diet ID, Inc., Detroit, MI (US)

(72) Inventors: David L. Katz, Hamden, CT (US);
Catherine S. Katz, Hamden, CT (US);
Rachna Govani, Birmingham, MI (US); Dina L. Aronson, Bloomfield, NJ (US); Lauren Q. Rhee, Fulton, MD (US); Austin Cameron, Louisville, KY (US); Udi Falkson, Brooklyn, NY (US)

(73) Assignee: Diet ID, Inc., Detroit, MI (US)

( * ) Notice: Subject to any disclaimer, the term of this patent is extended or adjusted under 35 U.S.C. 154(b) by 368 days.

(21) Appl. No.: 17/352,166

(22) Filed: Jun. 18, 2021

(65) Prior Publication Data
US 2021/0313039 A1    Oct. 7, 2021

Related U.S. Application Data

(63) Continuation-in-part of application No. PCT/US2019/067909, filed on Dec. 20, 2019.
(Continued)

(51) Int. Cl.
*G16H 20/60* (2018.01)
*G06F 16/432* (2019.01)
(Continued)

(52) U.S. Cl.
CPC .......... *G16H 20/60* (2018.01); *G06F 16/434* (2019.01); *G06F 16/50* (2019.01); *G06F 16/51* (2019.01);
(Continued)

(58) Field of Classification Search
None
See application file for complete search history.

(56) References Cited

U.S. PATENT DOCUMENTS

| 5,454,721 A | 10/1995 | Kuch |
| 6,553,386 B1 | 4/2003 | Alabaster |

(Continued)

FOREIGN PATENT DOCUMENTS

| TW | 201601089 A | 1/2016 |
| WO | 2016079719 A1 | 5/2016 |

OTHER PUBLICATIONS

Biltoft-Jensen-Jensen, A. et al., "Diet quality: associations with health messages included in the Danish Dietary Buidelines 2005, personal attitudes and social factors," Public Health Nutrition, vol. 12, No. 8, pp. 1165-1173 (Sep. 15, 2008).
(Continued)

*Primary Examiner* — Soo Shin
(74) *Attorney, Agent, or Firm* — McCarter & English, LLP

(57) ABSTRACT

Embodiments of the present disclosure are related to systems, methods, and computer-readable medium for image-based diet assessment. Image vignettes can form digital fingerprints that are derived from composite images of dietary patterns over a period of time, where the images can correspond to a grid of diet types and diet quality levels. Embodiments of the present disclosure include an image vignette generation and rendering process that is controlled based on a hierarchical algorithm and properties of the devices upon which the image vignettes are rendered.

19 Claims, 23 Drawing Sheets

Related U.S. Application Data

(60) Provisional application No. 62/782,773, filed on Dec. 20, 2018.

(51) Int. Cl.

| | | |
|---|---|---|
| *G06F 16/50* | (2019.01) | |
| *G06F 16/51* | (2019.01) | |
| *G06F 16/532* | (2019.01) | |
| *G06F 16/535* | (2019.01) | |
| *G06F 16/538* | (2019.01) | |
| *G06V 20/68* | (2022.01) | |
| *G09B 5/02* | (2006.01) | |
| *G09B 19/00* | (2006.01) | |

(52) U.S. Cl.
CPC .......... *G06F 16/532* (2019.01); *G06F 16/535* (2019.01); *G06F 16/538* (2019.01); *G06V 20/68* (2022.01); *G09B 5/02* (2013.01); *G09B 19/0092* (2013.01); *G06T 2207/30128* (2013.01); *Y10S 128/921* (2013.01)

(56) References Cited

U.S. PATENT DOCUMENTS

| | | | |
|---|---|---|---|
| 6,585,516 B1 | 7/2003 | Alabaster | |
| 7,558,788 B1 | 7/2009 | Herdman | |
| 8,738,432 B2 | 5/2014 | Hamilton, II et al. | |
| 8,777,624 B2 | 7/2014 | Klein | |
| 9,110,553 B2 | 8/2015 | Ash et al. | |
| 9,449,029 B2* | 9/2016 | Ting ........................ | G06F 16/56 |
| 9,892,501 B2 | 2/2018 | Dehais et al. | |
| 2001/0000810 A1 | 5/2001 | Alabaster | |
| 2002/0047867 A1 | 4/2002 | Mault et al. | |
| 2003/0059747 A1 | 3/2003 | Yoshida et al. | |
| 2003/0182160 A1 | 9/2003 | Lahteenmaki | |
| 2008/0275729 A1 | 11/2008 | Taggart et al. | |
| 2010/0080875 A1 | 4/2010 | Miller-Kovach et al. | |
| 2011/0318717 A1* | 12/2011 | Adamowicz ........... | G16H 20/60 |
| | | | 434/127 |
| 2012/0190386 A1 | 7/2012 | Anderson | |
| 2013/0027424 A1* | 1/2013 | Mochizuki ............. | G16H 40/63 |
| | | | 345/620 |
| 2013/0085345 A1* | 4/2013 | Geisner ................. | G06Q 30/00 |
| | | | 600/300 |
| 2013/0108993 A1* | 5/2013 | Katz ....................... | G09B 23/28 |
| | | | 434/127 |
| 2015/0205502 A1* | 7/2015 | Ubillos ................ | H04N 1/3877 |
| | | | 715/835 |
| 2015/0347520 A1 | 12/2015 | King et al. | |
| 2016/0035248 A1* | 2/2016 | Gibbs ....................... | G06T 7/60 |
| | | | 434/127 |
| 2016/0351072 A1* | 12/2016 | Nusbaum ........... | A63B 24/0062 |
| 2017/0128007 A1 | 5/2017 | Hayter et al. | |
| 2017/0243513 A1* | 8/2017 | Katz ...................... | G09B 29/00 |
| 2018/0267683 A1* | 9/2018 | Tessier .................. | G09B 5/065 |
| 2021/0313039 A1* | 10/2021 | Katz ......................... | G09B 5/02 |

OTHER PUBLICATIONS

Guenther, P. et al., Update of the Healthy Eating Index: HEI-2010, J. Acad. Nutr. Diet, pp. 1-21 (Feb. 2013).

Guenther, P. et al., Update of the Healthy Eating Index: HEI-2010, J. Acad. Nutr. Diet, vol. 113, No. 4, pp. 1-20 (Apr. 2013).

Hiza, H. et al., Diet Quality of Children Age 2-17 Years as Measured by the Healthy Eating Index-2010, U.S. Department of Agriculture, Nutrition Insight 52 (Jul. 2013).

Holm, L. et al., "Eating practices and diet quality: a population study of four Nordic countries," European Journal of Clinical Nutrition, vol. 69, pp. 791-798; entire document (Apr. 29, 2015).

Hungry Planet: What The World Eats, Time [Retrieved from the internet on Jun. 2, 2017 at http://Jworld.time.com/2013/09/20/hungry-planet-what-the-world-eats/photo/nor_ 130523_ 139_x/.] (Sep. 20, 2013).

Katz, D. et al., Can We Say What Diet is Best for Health?, Annu. Rev. Pub. Health, vol. 35, pp. 83-103 (2014).

Kim, S. et al., The Diet Quality Index-International (DQI-1) Provides an Effective Tool for Cross-National Comparison of Diet Quality as Illustrated by China and the United States, Journal of Nutrition, vol. 133, pp. 3476-3484 (2003).

Mailot, M. et al., "To Meet Nutrient Recommendations, Most French Adults Need to Expand Their Habitual Food Repertoire," The Journal of Nutrition, Nutrient Requirements and Optimal Nutrition, pp. 1721-1727 (Jul. 22, 2009).

Malagoli, C. et al., "Diet Quality and Risk of Melanoma in an Italian Population," The Journal of Nutrition, Nutrition and Disease, pp. 1800-1807 (Jun. 24, 2015).

International Search Report and Written Opinion from related International Patent Application No. PCT/US2019-067909 issued Mar. 25, 2020.

U.S. Appl. No. 17/739,593, filed May 9, 2022, Katz et al..

\* cited by examiner

Find your Diet ID

Choose again. You'll keep choosing until we identify your diet.

↺ Undo Previous Selection

Your personalized route

Here is how to reach your Diet IDEAL

Goals: Lose Weight, Decrease Inflammation and Improve overall health

Increase: Unsaturated (healthier) fats, Vegetables, Fruit, Fish decrease: Refined grains, Sweets & desserts, Shellfish, Full-fat dairy products

SYSTEMS AND METHODS FOR DIET QUALITY PHOTO NAVIGATION UTILIZING DIETARY FINGERPRINTS FOR DIET ASSESSMENT

RELATED APPLICATIONS

The present application is a continuation-in-part of International Patent Application No. PCT/US2019/067909, filed on Dec. 20, 2019, which claims the benefit of and priority from U.S. Provisional Application No. 62/782,773, which was filed on Dec. 20, 2018, each of which are incorporated by reference herein in their entirety.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

Good diet quality is a major contributing factor to the health and well-being of individuals and families, whereas poor diet quality is now established by the Global Burden of Disease study as the single leading predictor of premature death from all causes in the modern world. In order for individuals to manage their diets, and for health professionals to manage diet quality at scale, diet quality must be measured efficiently and routinely. No tool has been available to obtain information regarding current dietary intake of the individual and/or household and/or population with ease of use, time efficiency, economic efficiency, and accuracy.

Conventional dietary intake measures, including, for example, food frequency questionnaires, food diaries, and dietary recall, are notoriously prone to inaccuracies despite being very labor-intensive. They are, in fact, labor intensive for both the "client" and the professionals (i.e., dietitians, nutrition researchers) who rely on them for data. Because they are tedious, cumbersome, and not at all user-friendly, they are ill-suited to consumer-facing applications that are intended to be "inviting" or fun to use, such as apps on smart phones or other wearable technology (e.g. smart watches). They are equally ill-suited to fit into standard clinical or public health workflows, or for integration into electronic health records.

Food frequency questionnaires require that a user completes an extensive, detailed questionnaire document in paper or on-line format. Even then, the result is notoriously prone to inaccuracies due to the need to remember and estimate intake of diverse foods and choose representative foods from the inventory provided. Food diaries and 24-hour diet recall require the recording of foods at the time of consumption, or based on memory, and involve writing down details about foods and quantities and again require considerable time. A 7-day food diary may require hours of work. Finally, each of these methods requires individualized dietary analysis of the intake reported, generally involving specific software packages for nutrition analysis and a dietitian trained in their use to convert the reported intake of foods into information about intake of macronutrients and micronutrients.

Conventional, prevailing methods of dietary intake assessment, other than metabolic ward studies which are prohibitively expensive and inconvenient for routine application, typically require food-by-food and meal-by-meal narrative description of intake. An alternative method currently in development—the replacement of narrative descriptions with food photographs taken by the end user—again must assemble a representation of overall dietary pattern one food, dish, or meal at a time, and is dependent on the limits of image recognition software into the bargain. In addition, as discussed above, these methods either require real-time journaling, or depend on memory recall.

U.S. Pat. No. 6,585,516 to Alabaster, the subject matter of which is herein incorporated by reference in its entirety, describes a system and method for computerized visual behavior analysis, training and planning in which the user uses picture menus to choose meals for a particular time period to correspond to a customized eating plan. However, the picture menus consist of a series of instant meals that the user can mix and match at various nutritional, caloric, and other levels and can be used as a meal builder. In this instance, the user chooses the diet he wants to follow. However, the downside to this method is that the user must choose and build their meals for the day to meet a dietary goal, which can be a time consuming process. In addition, the user may not know what constitutes, a "good", "better" or "best" choice for a given category of foods or beverages. Most importantly, each image represents a meal, and is not representative of a dietary pattern. This system cannot be used to measure current dietary intake pattern, including type, quality, and nutrient composition.

U.S. Pat. No. 6,553,386 to Alabaster describes a computerized visual behavior analysis and training method in which the user interacts with a series of displays. A computer database includes information enabling display on a screen of objects, in successive groups, together with a display of graphics associated with each groups. The graphics allow a first user selection of one of the objects of each group and a second user selection related to the object selected by interaction with the screen display. The user selections may comprise food choices and evaluation of enthusiasm, and frequency thereof, so as to produce a dietary behavior profile. Diet training may then be coordinated by display of a meal and interactive adjustment of food items and portion sizes. This system cannot be used to measure current dietary intake pattern, including type, quality, and nutrient composition.

U.S. Patent Pub. No. 2017/0243513 to Katz, the subject matter of which is herein incorporated by reference in its entirety, is premised on the idea that dietary pattern can be expressed with a composite image, wherein each composite image depicts a unique inventory of proportions of foods, ingredients, dishes and meals representative of a particular diet quality level X as measured objectively of a particular diet type N as defined operationally for a period of time, which in one instance may be one week. In other words, the concept set forth by Katz is that a week is a sufficiently robust unit/time period to be "replicated" to establish a basic dietary pattern over a more meaningful interval, such as a year, or even a lifetime. With a representative dietary pattern for a week, 51 repeats of that pattern would constitute food intake for a year, and thus represent the approximate data retrieved in a traditional food frequency questionnaire. In this regard, Katz leverages the notion that a "picture is worth a thousand words" to avoid the many, tedious words required to complete a food frequency questionnaire. Instead, the user studies composite images, each representing a diet of given composition and objectively established quality over a period of a week (or any other suitable span of days) and selects the image representing the dietary pattern that most closely resembles his or her own. This method, called diet quality photo navigation, is predicated on dietary prototyping, mapping all diet prototype images by coordinates of Type-by-Quality, and achieving 'goodness of fit' for any given end user by situating them in the diet map.

SUMMARY

In image-based dietary assessment systems, the creation, storage, retrieval, and presentation of images as well as scaling and interpolation between images can be prohibitive and/or reduce both the efficiency and usability of a such image-based systems. As an example, composite images for dietary patterns can be crowded with elements of the dietary pattern making it difficult and/or overwhelming for user to interact with the system. As another example, whether the images are presented on a large display of a laptop or personal computer or the images are displayed by on a smaller display a mobile phone can affect the quality of the images rendered on the display as well as the users' ability to interface and interact with the images and the image-based system in a meaningful way. In this regard, it can be difficult to view composite images on smaller displays, e.g., such as displays of mobile phones or even smart watches or fitness trackers. As another example, there can be countless combinations and permutations of possible images to be stored and subsequently retrieved, which can require additional memory resources and processor resources. This can be particularly true when the images represent composite images corresponding to dietary patterns for an extended period of time (e.g., weekly or monthly dietary patterns), given different possible food elements and subtle changes to the dietary patterns represented by the composite images. Additionally, image-based systems typically scale by storing additional images, which increases memory usage and can cause the system to become unwieldy and slower.

Embodiments of the present disclosure provide several advantages that overcome the deficiencies associated with image-based dietary assessment systems, for example, by creating a database structure that facilities improved search and retrieval of images from the database; by reducing utilization of computer memory; by dynamically generating image vignettes that include less information than conventional composite images, but that can be mapped to unique dietary patterns associated with the composite images without sacrificing fidelity; by implementing a dynamic image generation process, and/or by dynamically adjusting the image generation and/or presentation process based on a type of display upon which the images are being rendered.

The advantages of embodiments of the present disclosure can be implemented, in an example application, to arrive at an identification of a user's current type of diet and level of diet quality in a more streamlined fashion and/or can generate intuitive image-based displays that replace inaccurate and tedious methods associated with conventional dietary intake methods. These advantages can also allow for a diagnostically valuable minimal set of elements captured by the created image vignettes to be retrieved and rendered in a graphical user interface on a display of a user and also allows the user to quickly and easily navigate through the images in the graphical user interface so that embodiments of the present disclosure can identify and/or analyze the user's current type of diet and level of diet quality and estimate the user's current caloric intake and nutrient level.

Furthermore, despite intense interest in technology-based methods of dietary intake data capture, such as smart phones, no such reliable method exists, and none is yet even in view. All such methods thus far envisioned still require active work by the end-user, and thus constitute a barrier to entry. In contrast, embodiments of the present disclosure replace this entirely with an application in which the user merely sequences through a series of image vignettes. That is, detailed dietary intake data can be generated for a user by navigating through the sequence of image vignettes and answering a few high level questions. No dietary intake data entry is required. These high level questions can include, for example, age, sex, height, weight, and habitual activity level (which can be selected from a standard ordinal scale).

The inventors of the present disclosure have unexpectedly determined that it is possible to identify quintessential elements of diet type and level of diet quality by depicting a single meal or small set of foods in an image vignette that is derived from a large composite image that depicts a unique inventory of proportions of foods, ingredients, dishes and meals representative of a particular diet quality level X of a particular diet type N for a period of time and/or that is derived from smaller elemental images that include individual foods, ingredients, and dishes. Accordingly, the inventors of the present disclosure have discovered that the image vignettes can be reduced to a minimal representation that is still representative of a particular diet. These derivative image vignettes can form unique "fingerprints" that identify particular diet quality levels and diet types of the users in an efficient and effective manner. Such "dietary fingerprints" map directly and exclusively to an overall dietary intake pattern of specific type and quality, just as a human fingerprint maps directly and exclusively to just one human being.

In accordance with embodiments of the present disclosure, a system, method, and computer-readable medium are disclosed for an image-based dietary assessment. A client device can include a client application and a server can include one or more processors for executing computer-readable instructions stored on a non-transitory computer-readable medium to implement operations of the method. The one or more processors can execute the instructions to query a first database to retrieve a set of elemental image files for a specified type of diet pattern. The first database can include records including elemental images and attributes associated with content depicted in the elemental images, where the content can include at least one of a food or a beverage. The attributes can define a type of diet pattern and define a quality of a diet pattern. The one or more processors can execute instructions to iteratively eliminate the elemental image files in the set of seed image files, based on the attributes stored in the database for the seed images, to define a selected subset of elemental image files and to extract elements from the elemental images in the subset of elemental image files. The one or more processors can execute the instructions to create a new image file defining an image canvas and insert the elements extracted from the elemental images into the image canvas at specified locations to generate an image vignette. The image vignette can incorporate at least two of the elements extracted from the elemental images in the subset of elemental images. The one or more processors can execute the instructions to store the new image file and create a record in a second database for the image vignette and associate the record with a specific diet type and diet quality level.

In accordance with embodiments of the present disclosure, a system, method, and computer-readable medium are disclosed for an image-based dietary assessment. A request for a sequence of images from a client device can be received at a server. The client device can include a client application and the server can include one or more processors for executing computer-readable instructions stored on a non-transitory computer-readable medium to implement operations of the method. The one or more processors of the server can execute instructions to query a database including a plurality of records including seed images and attributes associated with content depicted in the seed images to retrieve a set of seed image files based on information included in the request. The content of the seed images can include a least one of food or beverages. Each seed image is assigned a diet type and a diet quality level based on the attributes associated with the content of the seed images. The seed image files in the set of seed image files can be iteratively eliminated by one or more processors of the server executing the instructions, based on the attributes stored in the database for the seed images, to define a selected subset of seed images. Elements from the seed images in the subset of seed images can be extracted via the one or more processors of the server executing the instructions and one or more new image vignettes can be generated by the one or more processors of the server executing the instructions. Each new image vignette can incorporate at least two of the elements extracted from the seed images in the subset of seed images and the one or more image vignettes can be exported via the one or more processors of the server to the client device as the sequence of images in response to the request. A quantity of image vignettes that the server generates and exports can depend at least in part on a property associated with the client device. As an example, the property of the client device can be at least one of a size of a display of the client device, an available memory capacity of the client device, or a network connection speed at which the client device is operating.

In accordance with embodiments of the present disclosure, a temporary memory location can be allocated for storing the one or more image vignettes, instances of the one or more image vignettes can be stored in the temporary memory, and/or the instances of the one or more image vignettes can be deleted from the temporary memory by the server to deallocate the temporary memory location after the one or more image vignettes are exported.

In accordance with embodiments of the present disclosure, the one or more seed images can be at least one of a composite image depicts a unique inventory of proportions of foods, ingredients, dishes and meals representative of a particular diet quality level X of a particular diet type N for a period of time or an elemental images of integrated unit of foods or a beverage.

In accordance with embodiments of the present disclosure, the process of iteratively eliminating the seed image files in the set of seed image files to define a selected subset of seed images can include determining which of the seed image files in the set of seed image files satisfy a specified diet type based on attributes associate with the specified diet type and attributes associated with the seed images and eliminating the seed image files in the set that fail to satisfy the specified diet type from the set of image files; and/or determining which of seed image files remaining in the set of seed image files satisfy a threshold diet quality based on attributes associate with the specified diet quality and attributes associated with the seed images and eliminating the seed image files in the set that fail to satisfy the threshold diet quality. The process of iteratively eliminating the seed image files in the set of seed image files to define a selected subset of seed images can further include determining which of the seed image files remaining in the set of image files include prevalent elements associated with a specified dict type and eliminating the seed image files in the set that are devoid prevalent elements associated with the specified diet quality; determining which of the seed image files remaining in the set of image files include elements frequently consumed for the specified diet type and eliminating seed image files in the set that do not satisfy a specified frequency threshold; determining which of the seed image files remaining in the set of seed image files include elements that proportional contribute to the specified diet type by greater than a threshold proportion for the specified diet type and eliminating seed images files in the set that fail to satisfy the threshold proportion; determining which of the seed image files remaining in the set of seed image files include elements that are representative of the specified diet type and eliminating seed images files in the set of seed image files that are determine not to be representative of the specified diet type; determining which of the seed image files remaining in the set of seed image files include elements that differentiate the specified diet type other similar diet types and eliminating seed images files in the set that fail to satisfy a specified exclusivity threshold; determining which of the seed image files remaining in the set of image files include elements that have already been included in a threshold number of other image vignettes and eliminating seed images files in the set of seed image files that have been included in threshold number of other image vignettes; and/or determining which of the seed image files remaining in the set of image files include elements that can be alternatively inserted in the image vignette. The seed image files remaining in the set of seed image files that satisfy a minimum criteria for the image vignette after the seed files are eliminated from the set can form the subset of seed image files.

In accordance with embodiments of the present disclosure, a system, method, and computer-readable medium are disclosed for an image-based dietary assessment. A set of image vignettes for each diet type and diet quality combination can be generated by one or more processors. A first plurality of image vignettes can be iteratively rendered in a graphical user interface for selection by a user. Each of the image vignettes presents dietary characteristics of at least one of a different diet quality level or a different diet type. One or more first selections in the graphical user interface of one or more of the image vignettes from the first plurality of image vignettes can be received from the user. In response to receipt of the first selection in the graphical user interface, a second plurality of image vignettes can be iteratively rendered in the graphical user interface for selection by the user. The one or more processors can choose the second plurality of image vignettes to be rendered based on the first selection by the user such that the second plurality of image vignettes chosen by the one or more processors depends on the one or more first selections. The second plurality of image vignettes can include at least one image vignette that is different from the image vignettes in the first plurality of image vignettes. One or more second selections of one or more of the second plurality of image vignettes in the graphical user interface can be received from the user. In response to receiving the one or more second selections in the graphical user interface, a third plurality of image vignettes can be iteratively rendered in the graphical user interface for selection by the user. At least one of image vignettes in the third plurality of image vignettes is different from the second plurality of images vignettes. One or more third selections of one or more of the image vignettes in the third plurality of image vignettes in the graphical user interface can be received from the user. A user specific assessment of diet quality and type and an estimate of caloric intake and nutritional data can be determined by the one or more processors for the user based on the one or more first, one or more second, and one or more third selections. The one or more first selections can used to determine a diet type of the user and the one or more second and one or more third selections can be used to determine a diet quality level of the user. The user specific assessment of diet quality and type and the estimate of caloric intake and nutritional data can be rendered in the graphical user interface. An arrangement of the first, second, and third plurality of image vignettes in the graphical user interface can depend on a size and/or orientation of the display of the client device executing the client application.

Any combination and/or permutation of embodiments is envisioned. Other objects and features will become apparent from the following detailed description considered in conjunction with the accompanying drawings. It is to be understood, however, that the drawings are designed as an illustration only and not as a definition of the limits of the present disclosure.

DETAILED DESCRIPTION

Embodiments of the present invention provide an image-based systems, methods, and computer-readable media that can be employed for diet assessment and optimization. Embodiments of the image based system can be used to arrive at an identification of a user's current type of diet and level of diet quality and provide a user's goal type of diet and level of diet quality in a streamlined fashion and/or can generate intuitive image-based displays that replace inaccurate and tedious methods associated with conventional dietary intake methods.

Embodiments of the image based systems, methods, and computer-readable media can dynamically generate image vignettes (i.e., fingerprints) that can be derived from composite images and an image-based diet map representing the entire spectrum of real-world dietary patterns for a given population, encompassing both baseline diets, and goal diets for diverse health objectives. Like any map, the diet map is populated by coordinates, but rather than latitude and longitude, the diet map coordinates are 'diet type' by 'diet quality'. A unique image, representing a multi-day meal plan, can be formulated for each set of coordinates (i.e., cell in the map) by applying at a minimum two filters: DATs (differentiating attributes by type, that define food requirements, food exclusions, and food allowances for that given diet type) and DAQs (differentiating attributes by quality, defining the food elements concordant with the DATs that produce an overall eating patterns achieving a predefined score on the Healthy Eating Index 2015 scale). Each of these multi-day meal plan prototypes have been fully analyzed for nutrient and food group composition—at the "day" level and at the "dish" level. From these entries, the dietary fingerprint is derived as follows.

In order to dynamically generate an image vignette corresponding to fingerprint of a specific composite image, which is a quintessential representation of a multi-day meal plan, embodiments of the present disclosure can dynamically identify the best food dish (or beverage) combination from the total set of possible food dishes (or beverages) in underlying dietary intake meal plans and then dynamically assemble the image vignette as a composition of the best possible food dishes (or beverages).

Figure 1:
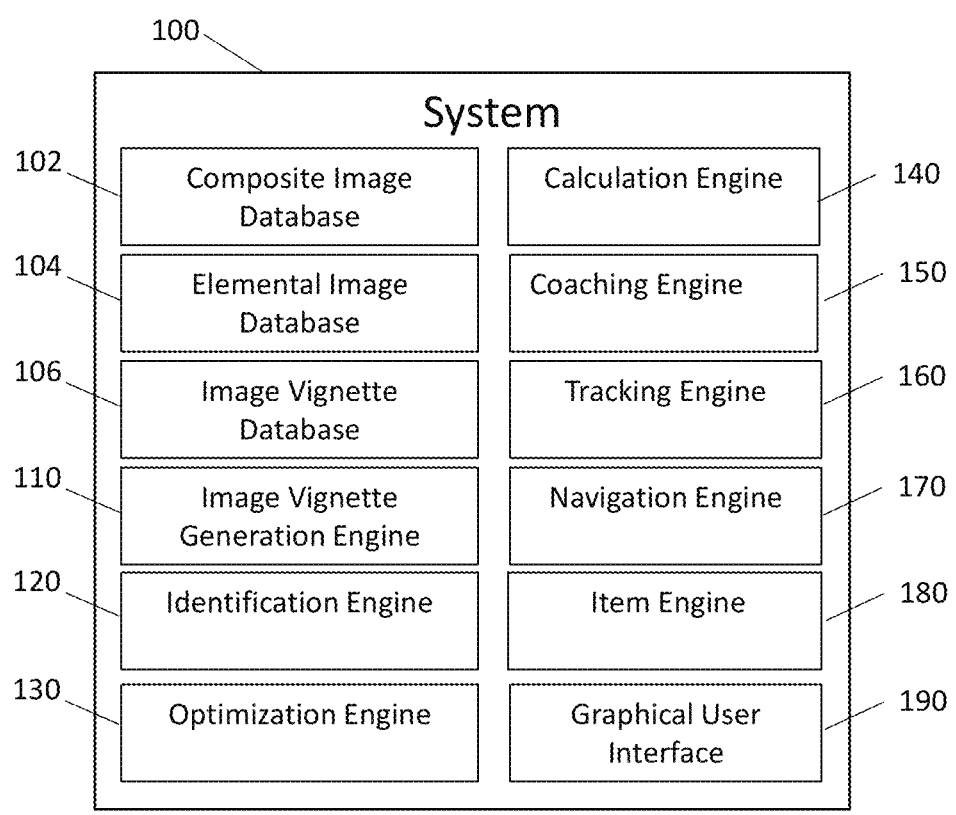
FIG. 1 is a block diagram of an image-based system in accordance with embodiments of the present disclosure.

FIG. 1 is a block diagram of an image-based system 100 in accordance with embodiments of the present disclosure. In an example application, the image-based system 100 can be implemented to facilitate dietary assessment and optimization. While an example application of the system 100 can be described with reference to dietary assessment and optimization, embodiments of the present disclosure can be implemented for other applications. The system 100 can include a composite image database 102, an elemental image database 104, an image vignette database 106, an image vignette generation engine 110, an identification engine 120, an optimization engine 130, a calculation engine 140, a coaching engine 150, a tracking engine 160, a navigation engine 170, an item engine 180, and a graphical user interface 190.

As described herein, composite images have previously been used for an example application of diet quality assessment and optimization to depict a unique inventory of proportions of foods, ingredients, dishes and meals representative of a particular diet quality level X of a particular diet type N for a period of time, which may be one week. Embodiments of the system 100 can provide for the dynamic generation image vignettes that form digital fingerprints of such composite images such that the visual representation provided by the image vignettes, although reduced, can replace the composite image to reduce the content being displayed and reduce the memory required to store images without significantly detracting from the accuracy and effectiveness of representing the content of the composite image. Users do not need to look at or study composite images of the full dietary pattern because the same, detailed knowledge of a user's dietary pattern can be reached via sequential presentation of the image vignettes, which are much simpler images to process, requiring less processing/computing time and greater case of use by the user. In the same way that a fingerprint represents much less than the full identity of a person but can be mapped to a single, unique identity, small, key features of dietary patterns can be used to map a user's dietary pattern.

To reduce the number of choices available to the user and streamline the process, filters can be used by the system 100 to identify diet preferences and diet restrictions. In one embodiment, other filters could also be used including, for example, where in the world are you and your diet? (region); basic diet character, and whether or not your diet is typical for that region; and so on. Applying just a few, high-level filters can reduce the relevant library for any individual to a much smaller, more easily navigated subset.

The system 100 can create an interface with the composite image library or database 102 that stores or references image files associated with composite images. For an example application of diet quality assessment and optimization, each composite image can be stored in the database 102 as a record and can depict a unique inventory of proportions of foods, ingredients, dishes and meals representative of a particular diet quality level X of a particular diet type N for a period of time (e.g., one week). The composite images can be photographs and can establish relative proportions of each variety of food so the quantitative representation of the food is accurate. The composite image database 102 can be structured as a grid or map where each record corresponding to a composite image is linked with or points to records that constitute the nearest neighbor. The diet types and diet quality levels can form a coordinate system for the map or grid. As one example, a record associated with a first composite image having a specified level X and type N can be linked with or point to records of a composite image having the same type N, but with level X that is incremented and/or decremented by one. As another example, a record associated with a first composite image having a specified level X and type N can be linked with or point to records of a composite image having the same level X, but with a type N that is incremented and/or decremented by one. Employing this grid-based architecture in the composite image database 102, advantageously allows the system 100 to identify not only a record of a specific composite image based on a query that includes a specified level X and a specified type N, but also allows the system to identify those records for additional composite images that are considered the nearest neighbor of the specific composite image. This can allow the system 100 to retrieve additional composite images without executing a query for the additional composite images (e.g., by retrieving images around the composite image in the map or grid). The structure of the composite image database 102 therefore allows the system 100 to not only pin point a specific composite image but to also target an area in the grid or map corresponding to a group of linked composite images associated with a diet type and/or a diet quality level.

To generate the composite image database 102, a validated measure of diet quality can be utilized to identify dietary patterns that each represent a level of diet quality for a period of time and a dietary score can be assigned to each of the dietary patterns. As a non-limiting example, validated measures such as the Healthy Eating Index or the Alternate Healthy Eating Index can be used. For example, the quintiles of the HEI can be used to identify a variety of "real world" dietary patterns representing a level of quality. The dietary score may be assigned to each of dietary patterns taking into account variations in region, culture, diet character and nutritional quality. The dietary patterns can be converted into representative dietary patterns. For example, the diet scores can be mapped back from nutrients, to food and beverage sources, and used to generate representative dietary patterns or "prototypes". Each such prototype can be readily displayed as "usual" food and beverages consumed, and these, in turn, can be composed into the subject of a composite image. The analytics and specifications for each of the diet types and diet quality levels of the representative patterns can then be calculated and the representative dietary patterns can be converted or translated into the composite images, which can be photographs, where each unique composite image depicts relative portions of foods, ingredients, and dishes for breakfast, lunch, dinner and snacks over a multi-day period, where the foods, ingredients, and dishes exemplify a level of diet quality X of an N diet type. The dietary patterns may include any of a number of typical dietary patterns for a given population, taking into account "poor," "good," "better," and "best diets for the given population.

The Healthy Eating Index (HEI), as explained, for example, in P.M. Guenther et al., "Update of the Healthy Eating Index: HEI-2010," Journal of the Academy of Nutrition and Dietetics, Dec. 21, 2012, is a measure of diet quality that assesses conformance to dietary guidelines for Americans. The HEI is routinely expressed in quintiles, i.e., 5 levels of diet quality. For convenience, these might be called: "poor," "fair." "acceptable," "good," and "excellent." In addition, there are a variety of specific dietary patterns that could qualify for each quintile based on its composition. Assignment to a given quintile is based on an overall quality score, which is in turn based on nutrient data, which is in turn based on customary food and drink intake reported.

Other validated measures of overall diet quality include the Alternate Healthy Eating Index (AHEI), developed at the Harvard School of Public Health as an 'alternate' to the original Healthy Eating Index developed at the USDA. The AHEI is more robustly correlated with health outcomes, including risk of any major chronic disease and all-cause mortality.

Any measure of diet quality, currently in use or yet to be conceived, can be used to develop the dietary patterns. For example, the dietary patterns can be selected from the group consisting of healthy eating index, alternative healthy eating index, healthy eating index 2010, alternative healthy eating index 2010, diet quality index, healthy eating index from food frequency score, healthy diet indicator, healthy food index, healthy food and nutrient index, recommended food score, diet quality score, diet quality, dietary guidelines index, Mediterranean diet score, Mediterranean adequacy index, alternative Mediterranean diet score, total and specific food group diversity, variations of any of the foregoing and combinations of one of more of the foregoing.

In some embodiments, the composite images in the composite images database 103 can be developed through an iterative process of 'tetrangulation' involving:

Diet Quality Expertise, in which a determination of Principal Differentiating Dietary Components (PDDCs) that differentiate among the quintiles of the HEI-2015 is made for any given variety of diet;

Diet Character Variant Expertise, in which researchers and dietitians with knowledge of real-world results in large epidemiologic studies will help establish parameters for range of variants for any given population;

Expertise in PDDCs, in which expertise in FACTOR ANALYSIS helps link salient dietary factors to differences of both character, and quality; and Expertise in food choreography, which uses creative oversight of food assemblies suitable for photography, with attention to food placement, emphasis, etc.

Each record in the composite image database 102 can result from input in these four areas, producing an inventory of foods suitable for photography.

To differentiate among diets that are much alike, food placement in the images can emphasize the subtle differences; and/or interactive programming can allow for magnifying subtle differences (e.g., by placing a cursor over an image, it's main differences from a neighboring image are highlighted in text, or by selectively pulling components into the foreground/magnification).

A grid of composite images is shown below in Table 1 as being illustrative of the expandable grid of diet quality.

TABLE 1

Illustrative Grid of Diet Quality

| SWD-1 | IWD-1 | AWD-1 | GWD-1 | EWD-1 |
|---|---|---|---|---|
| A | B | C | D | E |
| SWD-2 | IWD-2 | AWDv-2 | GWDv-2 | EWDv-2 |
| F | G | H | I | J |
| SWD-3 | IWD-3 | AWDv-3 | GVD | EVD |
| K | L | M | N | O |
| SWD-4 | IWD-4 | AWDv-4 | GAD | EAD |
| P | Q | R | S | T |
| SWD-5 | IWD-5 | AWDv-5 | GMD | EMD |
| U | V | W | X | Y |

(S = standard; I = improved; A = acceptable; G = good; E = excellent; WD = Western diet; WDv = variant on Western Diet; VD = Vegetarian diet; AD = Asian diet; D = Mediterranean diet)

The system 100 can create and interface with the elemental image library or database 104 that stores or references elemental image files associated with elemental images. For example, each record in the elemental database 104 can correspond to an elemental image. In addition to including or referencing the elemental image file, the record for each element image can include tags or data fields that include data or information related to attributes or characteristics of the content depicted in the elemental image. For an example application of diet quality assessment and optimization, the element images can depict integrated units of food or a beverage and the tags or data fields can include, for example, attributes associated with the integrated units of food or the beverage. An integrated unit of food can be a combination of food that forms a single, distinct dish. For example, an integrated unit of food can be toasted bread or can be a sandwich that includes bread, deli meet and cheese, but not to a meal which typically includes multiple integrated units of foods, such as a beverage, a main dish, and a side dish. The attributes can include defining attributes by type (DATs), such as key dishes, exclusions, inclusions, food group parameters, and/or nutrient parameters that may be used to define a type of dietary pattern; defining attributes by quality (DAQs), such as exclusions, inclusions, food group parameters, and/or nutrient parameters that may be used to define a quality of a dietary pattern; a prevalence define by population-level data, such as a prevalence of specific dish or beverage categories, which can be derived from published materials and nutritional epidemiology; a frequency with which a dish or beverage appears in a specific diet type; and a proportional contribution indicating contribution of an ingredient, dish, or beverage to an overall diet type by volume or energy.

As a first step in the process for creating the elemental image database 104, food dishes in a multi-day meal plan (representative of a typical prototypical way of eating, defined by a specific diet type and a diet quality level) are identified. A multi-day meal plan can consist of breakfast, lunch, dinner, snacks, and beverages per day. A multi-day meal plan can be generated with fixed entries, or can be dynamically generated with an array or entries. Each food dish has a corresponding visual representation. For example, if one "Breakfast" in a multi-day meal plan is a bagel with cream cheese, the elemental image database can store an isolated image of a bagel with cream cheese which corresponds to an integrated unit of food. This isolated elemental image may be composed of two components, e.g. the bagel as one component and the cream cheese as a second component. The two components can be used to create one single Breakfast image.

Each isolated dish image (elemental image) is tagged with the diet type and diet quality level meal plan from which it originated. For example, if the bagel with cream cheese was found in the multi-day meal plan of the American Style, Quality Level 2 meal plan on day 2, the image would be tagged with "Type=American," "Quality Level=2." "Meal=Breakfast," "Day=2."

The system 100 can create and interface with the image vignette database 106 that stores or references image vignette files generated by the system 100 based on the composite images of the composite image database 102 and/or based on the elemental images of the elemental image database 104. Each record in the image vignette database 106 can reference or point one of the composite images in the composite image vignette database 102 to map the image vignettes to the grid defined by the composite image database such that each image vignette corresponds to a specific diet level X and data type N for the example application of diet quality assessment and optimization. In some embodiments, the image vignettes can be stored with their corresponding composite images in the composite image database 102, rather than having a separate image vignette database 106.

The image vignette generation engine 110 can generate image vignettes based on the composite images of the composite image database 102 and/or based on the elemental images of the elemental database 104. In some embodiments, the image vignette engine 110 can generate at least one image vignette for each composite image of the composite image database 102 or for each possible combination of diet quality level X and diet type N. The image vignettes can be assembled by populating an image vignette file with elements that (a) collectively map to, and exclusively to, a single cell in the diet map (i.e., a particular diet type and diet quality level); (b) capture and convey the general character of that dietary pattern at a glance; (c) allow the end user to choose or reject that 'dietary fingerprint' as their own, based on rapid pattern recognition. The image vignette generation process can be standardized by the image vignette generation engine to eliminate the 'visual burden' of distraction by movement in dietary components. For example, the image vignette generation engine can define standardized placement locations for discrete dietary components (e.g., beverages are always located in the same location for each image vignette) permits undistracted attention to compositional changes, without changes in placement.

The image vignettes generated by the image vignette generation engine 110 can be stored in the image vignette database 106 for subsequent use and can be linked to records for the composite images in the composite image database 102. In some embodiments, once the image vignette database 106 is created and include at least one image vignette for each composite image, the system 100 can delete the composite images, while maintaining the grid of the level and type. In some embodiments, the image vignette engine 110 can generate image vignettes on demand in response to input received from a user. The image vignettes generated on demand can be temporarily stored by the system 100 until they have been exported to a client application being executed on a client device, at which time the system can delete the image vignettes. For embodiments that utilize on-demand generation of image vignettes, the system 100 may be devoid of the image vignette database 106. Using this approach, the system 100 can actively manage memory allocation to decrease amount of memory required to store images. The effect of this approach can be useful as the number of possible image vignettes increases based on an increase in the number composite images and/or elemental images stored in the databases 102 and/or 104, respectively, because the system 100 does not have to allocate dedicated memory resources to the image vignettes.

The image vignettes can form "dietary fingerprints" which are a composed assembly of food images used to identify the particular diet quality level and diet type of the user in an efficient manner. The compositions captured in the image vignettes can characterized as "fingerprints" because they function as human fingerprints do: a very tiny portion of the whole can be mapped reliably, and exclusively, to the one "whole" it represents. In the case of human fingerprints, that is a person; in the case of dietary fingerprints, that is a specific, operationally defined type of dietary intake pattern at a specific, objectively quantified tier of overall nutritional quality. In some embodiments, each of these unique image vignettes can be derived from a corresponding unique composite image and/or a 3-day meal plan for that corresponding "cell" in the diet map or grid (a prototype of a distinct diet type and quality level). For example, the image vignettes can be visual representations of a prototypical 3-day meal plan for that particular diet quality level and diet type.

In this regard, each image vignette can represent signature food characteristics of the particular diet quality level X of diet type N, which may include a small number of foods that most accurately reflect both the particular diet quality level X and particular diet type N. In one embodiment, this small number of foods may include approximately three to about ten foods, or four to eight foods, but may be any number that can accurately reflect the characteristics in a simple and straightforward manner. For example, a "worst case" low diet quality level of an image vignette of an "American" diet may include images of soda, pizza, french fries, bacon, cookies/desserts and be devoid of vegetables. On the other hand, a "high quality" high diet quality level of an image vignette of a Mediterranean diet may include images of steel cut oats, salad, fish, fruits/vegetables, non-fat yoghurt and water.

In embodiments of the system 100, the image vignette generation engine 110 can generate the image vignettes from the composite images. The image vignette generation engine can query the database of composite images and retrieve an image file that corresponds to a specific composite image from memory based on the tags in the database. As an example, the query can include the coordinates of the specific composite image in the grid having a specified diet type and diet quality. The image vignette generation engine 110 can perform one or more imaging processing and/or machine vision to process the composite images and extract element from the composite images. For example, the image vignette generation engine 110 can use Stitching/Registration, Filtering, Thresholding, Pixel counting, Segmentation, Inpainting, Edge detection, Color Analysis, Blob discovery and manipulation, Neural net processing, Pattern recognition, Optical character recognition, blurring, normalized lighting, greyscaling, OTSU, thresholding, erosion/dilation, convert correct hull, contour detection, blob/mass calculation normalization, and/or Gauging/Metrology to extract elements from the composite image based on, for example, the hierarchical algorithm described with reference to FIG. 9. The image vignette generation engine 110 can create a new image file corresponding to an image vignette to be generated based on the extracted elements, where the new image file defines an image canvas. The image vignette generation engine 110 can insert the extracted elements from the image file for the composite image into the image canvas of the new image file at specified locations.

In embodiments of the system 100, the image vignette generation engine 110 can generate the image vignettes from the elemental images. The image vignette generation engine can query the elemental images database to retrieve a set image files from memory corresponding to elemental images based on the tags in the elemental image database. As an example, embodiments of the system 100 can generate one or more queries for elemental images having tags that correspond to one or more specified dietary patterns. The image vignette generation engine 110 can select a subset of the image files based on a hierarchical algorithm described herein that receives as an input the tags associated with the elemental images. As an example, the one or more processors can execute the hierarchical algorithm to iteratively eliminate image files from the set of retrieved image files based on the tags associated with the elemental images associated with the image files as described herein, e.g., with reference to FIG. 9. Once the subset of elemental images is created, the image vignette generation engine 110 can extract the elemental images from the image files associated with the subset of the selected elemental images insert the extracted elemental images from the image files of the subset into an image canvas of a new image file created by the image vignette generation engine 110. As described herein the elemental image can be inserted into the image canvas at specified locations.

Each multi-day meal plan (e.g. Y-day meal plan) for each cell in the diet map for the composite images consists of the following:
Y breakfasts
Y lunches
Y dinners
Y or more beverages
Y or more snacks Each dietary fingerprint represented by an image vignette incorporates a set of Z number images arranged into a standardized architecture, and can consist of at least one of the following items, one in each slot in the image vignette.
Breakfast
Lunch
Dinner
Beverage
Snack In order to dynamically identify the best Z number of dish (or beverage) images (elemental images) from the total array of images from the Y-day meal plan, the image vignette generation engine 110 can utilize hierarchical series of inter-dependent filtering algorithms illustrated by the below table and described in more detail with reference to FIG. 9.

| | |
|---|---|
| DATs (Defining attributes by type, e.g. key dishes, exclusions, inclusions, food group parameters, and/or nutrient parameters) | Entry must be compatible |
| DAQs (Defining attributes by quality, e.g. exclusions, inclusions, food group parameters, and/or nutrient parameters) | Entry must be compatible |
| Prevalence (Defined by population-level data about prevalence of specific dish categories, derived from published materials and nutritional epidemiology) | Prioritize entries eaten by 'nearly everyone' in given population |
| Frequency (Defined as a frequently occurring dish, beverage, or "entry" in our cells.) | Prioritize entries eaten most often in the DietType and/or the Diet Quality Level |
| Proportional contribution | Prioritize entries making largest proportional contribution to overall diet type by volume or energy |
| Representativeness | Prioritize entries most strongly associated with diet type (e.g., foods most 'integral' to DATs) |
| Exclusivity | Prioritize entries that best differentiate between a given diet and its neighbors in the diet map |
| Redundancy | Establish upper bounds for entry recurrence. IF already display X times, THEN suppress at X + 1 IF there is a suitable alternative, ELSE IF there is no suitable alternative, then display X + 1st time. |
| Reciprocals/Alternativality | If entries A and B work for a given cell in sequence, but only B works for higher quality cells, then prioritize A as initial selection. |

Using the above algorithm, the image vignette generation engine 110 can select a specified number of elemental images for a specified number of slots in the image vignette to be created. For example, the image vignette generation engine 110 select eight food dishes represented by the elemental images that can be used to form the image vignette (e.g. one breakfast dish, two snacks, two dinner dishes, two lunch dishes, and a beverage). The image vignette generation engine 110 can form the image vignettes so that each category of dish (e.g., breakfast, lunch, dinner, snack, beverage) are always located in the same area of the image vignettes so that slight changes from one image vignette to another image vignette can be readily perceived by a user. To achieve this, the image generation engine 110 can resize the content extract from the elemental images to fit within the designated area so that the scale between content represented by each elemental image is maintained.

The system 100 can be programmed and/or configured to adapt the image vignettes to the display device upon which the image vignettes are to be rendered based on a property of the client device In this regard, the system 100 can control the process for generating and rendering the image vignettes in a graphical user interface of a client application on a client device. As an example, a number of image vignettes generated and exported by the system 100 for each iteration can be dependent on one or more properties of the client device, such as an available memory capacity, a network connection speed, a type of display technology, a size of screen of the display, a resolution of the display, and the like. The system 100 can determine the one or more properties of the client device based on communication with the client device. More image vignettes can be generated and/or exported for larger screens or device with more available memory and fewer image vignettes can be generated and/or exported client device with smaller screens or less available memory. As another example, both the size and the number of images visible in the screen can be dynamically adjusted by the image vignette generation engine. On a larger screen, the image vignettes can be displayed side by side, while on a smaller screen (such as a smart phone screen), the image vignettes can be displayed vertically (one above the other) if the smaller screen is detected to be held in a portrait viewing orientation or can be displayed side-by-side if the smaller screen is detected to be held in the landscape viewing orientation. For even smaller screens, such as on a smart watch, the system 100 alternate displaying among the image vignettes. In addition, depending on the size of the screen, certain functions, such as the ability to navigate to composite image corresponding to an image vignette and/or the ability to hover over an image vignette to initiate a magnifying glass function to zoom in on a portion of the image vignette can be disabled. While the number of derivative image vignettes displayed may be any number greater than 1, it is contemplated that the number of images displayed will be between 2 and 50 images, more preferably between 3 and 20 images, and even more preferably between 4 and 10 images. In one embodiment, the number of derivate image vignettes displayed on the graphical user interface is 2.

The identification engine 120 can be programmed and/or configured to present image vignettes to a user by rendering the image vignettes in a graphical user interface on a client device being operated by the user. Initially, the identification engine 120 can generate and/or select one or more sets of image vignettes (associate with different levels and/or types) to display to the user, where the user can select image vignettes from the sets and the identification engine 120 can use the selections converge on one of image vignettes as a starting point of the user (e.g., a starting level and type). For an example application of diet quality assessment and optimization, the identification engine 120 can determine, based on the user's selection of one or more image vignettes via the graphical user interface, the user's current/baseline diet quality level X and current/baseline diet type N. The identification engine 120 can calculate/identify a dietary score for the user based on the selected image vignettes, which can be rendered in the graphical user interface to display the dietary score to the user. The closest approximation to the subject's dietary pattern from the entire library of composite images (best fit) can be identified based in the selection of the image vignettes. This dietary pattern corresponds to specific, well-known nutrient intake levels/1000 kcal.

In one embodiment, the identification engine 120 can render a sequence of image vignettes that correspond to the four corners of the grid or map in the graphical user interface to depict extremes in "best" and "worst" types and levels of diet quality.

The optimization engine 130 can be programmed and/or configured to present image vignettes to a user by rendering the image vignettes in a graphical user interface on a client device being operated by the user. The optimization engine 130 can be executed after a starting point has been identified by the identification engine 120. The optimization engine 130 can generate and/or select one or more sets of image vignettes (associate with different levels and/or types) to display to the user, where the user can select image vignettes from the sets and the identification engine 120 can use the selections converge on one of image vignettes as an end point of the user (e.g., an end level and type). For the example application of diet quality assessment and optimization, the optimization engine 130 can determine, based on the user's selection of one or more image vignettes via the graphical user interface, the user's end/goal diet quality level X and end/goal diet type N. The optimization engine 130 can also comprise a personalization module 132 through which a user can identify one or more elements of diet to be added, reduced or removed from their diet, including alcohol/wine, meat, poultry, seafood, etc.

For the example application of diet quality assessment and optimization, the calculation engine 140 can be configured to calculate personalized nutrient levels and personalized environmental impacts of the user based on information input by the user via the graphical user interface, wherein the graphical user interface includes data entry fields to receive the input of the information from the user and data output fields to display the calculated personalized nutrient levels to the user. The input may include, for example, personalization information containing the level of diet depicted in the series of images, dietary restrictions, personal information of the user (i.e., gender, age, height, weight, etc.), activity level of the user, and other information, and can obtain additional guidance, related, for instance, to recommended calorie intake; serving sizes; etc.

The calculation engine 140 can then calculate personalized nutrient levels of the user based on the image vignettes selected and the input information and then display this information to the user via the graphical user interface. The calculation engine 140 can calculate a user specific assessment of diet quality and type for the user based on the selected image vignettes and can display the calculated user specific assessment of diet quality and type to the user in the graphical user interface.

The calculation engine 140 can also quantify the user's nutrient intake to establish a habitual calorie level. For example, the user's nutrient intake to establish a habitual calorie level calculated with height, weight, sex, age, and activity level, using metrics such as the Harris-Benedict or Mifflin-St. Jeor equations (and, or, any other suitable methods) for determining basal metabolic rate. Using this approach, the calculation engine 140 estimates total calorie requirements for a user, and can adjust the dietary parameters from the assessment to right-size" the diet for the user such that the diet is personalized for the user. In some embodiments, information related to energy expenditure of a user (e.g., from physical activity) can be captured view one or more devices (e.g., wearable device, such as smart watches, heart rate monitors, fitness trackers, etc.) worn by the user. These connected devices can be connected (either wirelessly or wired) to the client device of the user and the information collected by these devices can be used by the calculation engine 140 when establishing personalized nutrient parameters and/or caloric parameters for the user. Embodiments of the system 100 can determine a specific diet type of the user; determine a specific diet quality of the user; and can customize or personalize (right-size) the dietary assessment as well as the steps required by the user to optimize their diet to achieve a goal diet type and quality level.

The coaching engine 150 can be populated with and coaching tips corresponding to discrete steps and changes a user can follow to move from one type N to a different type N and/or from one level of quality X to a different level of quality X. The coaching engine 150 can selectively render the coaching tips in the graphical user interface to display the coaching tips to the user. For an example application of diet quality assessment and optimization, the coaching engine 150 can selective provide coaching tips corresponding to discrete steps and changes to allow the user to modify their diet from one diet type N to a different diet type N and/or from one level of diet quality X to a different level of diet quality X. In some embodiments, the coaching tips can provide discrete/incremental steps/changes that may be taken by a user to move from an initial level of diet quality X to a different level of diet quality X. Upon converging on an image vignette to establish a starting point, the coaching engine 150 can render one or more coaching tips in the graphical user interface to display the one or more coaching tips to the user, where the coaching tips describe a step-wise fashion for incrementally changing the diet from a first/baseline diet N and level of diet quality X to a different diet type N and/or level of diet quality X. The coaching tool 150 may be configured to provide substitute or complementary items to the user. Some examples of coaching tips include:

Type of diet: American (highly processed)→flexitarian→Mediterranean→vegetarian→vegan Meat: Red meat→Grass-fed read meat→Red meat once/week→Red meat once/month→Red meat rarely Poultry: Chicken/poultry→Free range→Organic→Substitute one or more meatless meals Fish: Farm-raised→wild caught→particular types of fish Produce: Eat more vegetables/fruits→refined/processed→canned→frozen greenhouse grown→organic→field grown→in season Shopping: Supermarket→farmer's market→community sponsored agriculture (CSA)→home garden Packaging: Processed→canned→plastic-wrapped→cardboard→minimal→none Origination of goods: International→regional→local→home garden Level of refinement: heavily processed→canned→frozen→fresh→organic The tracking engine 160 can provide a graphical user interface that allows the user to change, update, or view the type N and the level of quality X currently assigned to the user; change or update the type N and the level of quality X corresponding to the end point; and/or compare changes in type N and level of quality X assigned to the user over time. For example, the graphical user interface can display an input screen to allow the user to change, update, or view their diet type N; change, update, or view their level of diet quality X, and can display changes in level of diet type N and level of diet quality X assigned to the user over time.

The navigation engine 170 can be generate discrete steps to move the user stepwise from one level of quality X of one type N to a different type N and/or from one level of quality X to a different level of quality X. The navigation engine 170 can render a navigation route in the graphical user interface showing the user how to advance from the starting point/baseline to the end/goal point. The navigation route can be rendered as a sequence of the image vignettes corresponding the levels of qualities X and/or types N between the starting point and the end point. For example, the navigation route or navigation steps rendered in the graphical user interface by the navigation engine 170 can provide a stepwise route the user can follow from one diet type N to a different diet type N and/or from level of diet quality X to a different level of diet quality X.

For the example application of diet quality assessment and optimization, the item engine 180 can be configured to provide a grocery list for a user and information about the items on the grocery list for the user. The items may be listed on a manufacturer's or merchant's website or on other websites. Additional information, such as "green" information, may be obtained about an item. For example, selecting the item may also give descriptive information, for example by a hyper-link to green information on the website or on the world wide web or Internet. The item engine 180 may also be employed to provide a profile which may be used to specify what characteristics of items are to be displayed.

The graphical user interface 190 can be configured to provide one or more graphical user interfaces (GUIs) through which users of the system 100 can interact with the system 100. The GUIs can be rendered on display devices and can include data output areas to display information to the users as well as data entry areas to receive information from the users. For example, data output areas of the GUIs can output image vignettes as well as information associated with a user, such as diet score, nutrient and calorie calculations, navigation paths/routes, item lists, and the like, and the data entry areas of the GUIs can receive, for example, information associated with the users. Some examples of data output areas can include, but are not limited to text, graphics (e.g., graphs, maps (geographic or otherwise), images, and the like), and/or any other suitable data output areas. Some examples of data entry fields can include, but are not limited to text boxes, check boxes, buttons, drop-down menus, scroll bars, hyperlinks or other selectable links, which may be embedded for example in one or more image vignettes, and/or any other suitable data entry fields.

In some embodiments, the graphical user interface 190 can provide an input screen to allow the user to input personal information about the user in the graphical user interface 190. For example, the graphical user interface 1900 can allow the user enter information regarding dietary restrictions or dietary preferences prior to or after being presented with the display of the image vignettes or at any time there between. In some embodiments, at least some of the information can be automatically obtained such that the user is not required to manually enter the information. As one example, the system 100 can receive geographic location information from a location enabled client device (e.g., a smart phone or other GPS enabled device) of the user based on GPS coordinates of the client device and/or can estimate the geographic location of the user based on an Internet Protocol (IP) address through which the client device is communicating. The geographic location can be used to narrow reduce the relevant library of image vignettes to start from for any individual to a much smaller, more easily navigated subset. As another example, information related to a user's physical parameters and energy expenditure can be collected for user by the system 100 through one or more connected devices (e.g., wearable device, such as smart watches, heartrate monitors, fitness trackers, etc.) which can be connected to the client device (either wirelessly or wired). Such information can be used by the system 100 when personalizing "right-sizing" a user's diet. Using the information input by the user or automatically provided via the client device or associated connected devices, the graphical user interface can be populated with a first set of image vignettes for selection by a user on a graphical user interface that are appropriate for the user based on their dietary restrictions and/or dietary preferences.

The input screen can allow the user to input diet modification information, such as dietary preferences regarding specific ingredients, dishes, meals and/or foods and the input screen can allow the user to input additions or subtractions in whole or in part of these specific ingredients, dishes, meals and/or foods. These dietary preferences may include one or more of alcohol, meat, poultry, fish, nuts, water, dairy, vegetables, fruits, refined grains, whole grains, legumes, fast food, sweets, and alcohol. This diet modification information may also comprise dietary restrictions such as dairy-free, gluten-free, shellfish-free, peanut-free, egg-free, nut-free, wheat-free, soy-free and alcohol-free and the input screen allows the user to input the dietary restrictions.

In some embodiments, the graphical user interface 190 can present the user with one or more queries to answer some baseline or intake questions so that the first set of images vignettes displayed is tailored to dietary preferences of a user. For examples, these queries may analyze whether a user cats meat or cats grain products. Thus, in the case of a user indicating that they are vegetarian or vegan, the first set of derivative images would be plant-based, and the user would not be presented with any meat-based derivative image vignettes during the selection process. Thus, a few simple on-boarding questions (i.e., "do you eat meat?"; "where in the world are you" (region); basic diet character; and whether or not your diet is typical for that region; and so on.) are processed by the system 100 to determine which image vignettes to initially display in the graphical user interface 190 to the user.

In one example operation, the system 100 renders a first set of unique image vignettes of diet quality levels $X_n$, in the graphical user interface for selection by a user. Upon selection by the user of one of the unique image vignettes in the first set of unique image vignettes, the system 100 can render a different plurality of unique derivative image vignettes of diet quality levels $X_n$ in the graphical user interface for selection by the user. For example, if the user is first presented with images $X_1$ and $X_2$ and selects image $X_2$, the user may then be present with images $X_2$ and $X_3$. If the user selects image $X_3$, the user may then be presented with images $X_3$ and $X_4$. If the user again selects image $X_3$, the selection process may stop, whereas if the user selects image $X_4$, the iterative process may continue until the processor determines that the selected derivative image vignette most closely resembles the user's current diet quality level X of diet type N. The system 100 can use this image vignette selection process to determine a current diet type and a current diet quality of the user and/or can use this image vignette selection process to determine a goal diet type and a goal diet quality level for the user. Once the system 100 determines the diet type and diet quality of the user, the system can further personalize the diet quality assessment of the user and/or personalize a diet plan for the user to help the user reach the user's goal diet type and quality level. For example, the system 100 can "right size" the users diet based on personal information provided by the user and the determined current and/or goal diet type and the current and/or goal diet quality using for example, metrics such as the Harris-Benedict or Mifflin-St. Jeor equations (and, or, any other suitable methods)

In one example operation, once the image vignettes are generated by the system 100 as described herein, a sequence of image vignettes can be rendered in a graphical user interface 190 on the display of a client device. The graphical user interface 190 can include a first scroll bar associated with a first set of derivate image vignettes rendered in the graphical user interface for selection by the user. Each image vignette in the first set can depict dietary characteristics of a particular diet quality level X of a particular diet type N. The first set of image vignettes associated with the first scroll bar can comprise image vignettes depicting a range of quality levels X of a range of diet types, e.g., $X_a N_b$ to $X_{a+n} N_{b+m}$, wherein $X_a$ represents a lowest diet quality level of the range and $N_b$ represents a lowest quality diet type rendered in the first set, and wherein $X_{a+n}$ represent an improvement in diet quality that is "n" degrees away from the diet type represented by $X_a$ in the grid and $N_{b+m}$ represents a diet type that is "m" degrees away from the diet type represented by $N_b$ in the grid. The values of n and m can each represent a number greater than or equal to one. Upon selection of one of the image vignettes associated with the first scroll bar by the user, a secondary scroll bar can be rendered in a graphical user interface on the display of the client device that is associated with a second set of image vignettes for selection by the user. At least one of the image vignettes in the second set of image vignettes can be different from the image vignettes in the first set image vignettes. In response to selection of one of the image vignettes in the second set of image vignettes associated the secondary scroll bar by the user, the system 100 executed by the one or more processors determines the user's specific type of diet. Once the system 100 determines the diet type, in response to selection of one of the image vignettes in the second set, a third set of image vignettes can be rendered in the graphical user interface and can be associated with a tertiary scroll bar. At least one of the image vignettes in the third set of image vignettes can be different from the image vignettes in the second set of image vignettes. In response to selection of one of the image vignettes in the third set of image vignettes associated with the tertiary scroll bar by the user can be used by the processor executing the system 100 to determine the user's specific level of diet quality. The graphical user interface rendered on the client device can allow a user to input personal information about the user and the system can calculate a user specific assessment of diet quality and type and estimate of caloric intake and nutrient data for the user. The calculated user specific assessment of diet quality and type and estimate of caloric intake and nutrient data can be rendered in the graphical user interface.

In some embodiments, the first scroll bar includes image vignettes that are representative of the most extreme "worst" diet quality levels of particular diet types and the most extreme "best" diet quality levels of particular diet types and other varying diet quality levels of particular diet types. By being presented with extremely different types of diets and levels of diet quality, this first scroll bar enables the user to make an initial selection of a type of diet and level of diet quality that reflects the character of their diet. Secondary scroll bars and tertiary scroll bars can then be used to refine this initial selection to hone in on a closer approximation of the type of diet and level of diet quality of the user and the user may cycle through these secondary and tertiary scroll bars multiple times if needed to reach the "best fit" of an image vignette that most closely approximates their diet type/level or diet quality. It is also noted that the user only cycles through the derivative image vignettes displayed on the graphical user interface but is not "guessing" their own level of diet quality or type of diet. It is the selection of the image vignettes by the user that allows the processor executing the system 100 to determine the user's type of diet and level of diet quality based on the images selected.

This information can then be personalized to the user by providing an input screen in which the user can input personal information regarding the user and this personal information personal information may comprise one or more of gender, age, height, weight, and activity level.

In some embodiments, the system 100 can be programmed and configured to render the image vignettes in the graphical user interface as a fingerprint corresponding to the larger composite image for the particular diet type and diet quality level. The user can access a particular composite image associated with a particular derivative image vignette (e.g., by selecting an option in the graphical user interface 190 to view the corresponding composite image). In some embodiments, the function that allows the user to view a composite image corresponding to an associated image vignette can be disable by the system if the system 100 determines that a size of the display upon which the graphical user interface 190 is being rendered does not satisfy a threshold size and can be enabled when the system 100 determines that the size of the display does satisfy the threshold size. In some embodiments, the function that allows the user to use a magnifying glass function to hover over a portion of an image vignette to magnify that portions can be disable by the system if the system 100 determines that a size of the display upon which the graphical user interface 190 is being rendered does not satisfy a threshold size and can be enabled when the system 100 determines that the size of the display does satisfy the threshold size. As an example, the system 100 can disable the function when the graphical user interface is rendered on a display of a mobile phone and can enable the function when the graphical user interface is rendered on a display of a laptop or personal computer.

In some embodiments, the system 100 can be linked to a fitness interface, so that a user is receiving guidance for diet and physical activity improvements concomitantly. While this is optional, in this mode, the diet tips provided can be adjusted to address the physical activity pattern and goals. Furthermore, an interactive system can be used to "plug in" to the system 100 described herein to provide access to recipes/options.

It is specifically contemplated that user selections and/or the results gleaned from the present disclosure may be in communication with third party servers or applications. According to the present disclosure, an interactive system may further include a step counter/pedometer. When a user walks or jogs, the present disclosure may inform the system of the total amount of calories that a user has expended, and the interactive system may inform the amount of calories a user has consumed or the quality of the diet consumed. It is contemplated that the present disclosure may compare expended and consumed calories. A remote server and communication means may connect the above systems to each other. The present disclosure may further include storage or memory for storing nutrition information, nutrition/energy taken, the nutrition/energy expended. A user may input the nutrition facts/energy into the storage through a keypad or other methods.

Because dietary intake assessment with the process described herein is almost instantaneous, nearly effortless, and potentially even fun, the process described herein allows for limitless applications in apps, interactive websites, and games. Identification of a "goal" diet is as streamlined as identification of baseline diet and with attention to the incremental dietary changes along the way from baseline to goal, the process described herein is designed to identify key, desirable dietary changes; to address these changes in a logical sequence; and to "coach" the process of dietary change. The platform can function in this manner on its own (i.e., app, website, wearable health tech) or can be used by to enhance the guidance of a human health coach.

As will be appreciated by one skilled in the art, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product embodied in any tangible medium of expression having computer-usable program code embodied in the medium.

The system 100 can include computer program code for carrying out operations of the present disclosure may be written in any combination of one or more programming languages, including an object-oriented programming language such as JAVA, SMALLTALK, C++ or the like and conventional procedural programming languages, such as "C" or similar programming languages as well as one or more scripting languages, such as Python, JavaScript, Rails, Ruby, and the like. The program code may execute entirely on the user's computer, partly on the user's computer, as a stand-alone software package, partly on the user's computer and partly on a remote computer or entirely on the remote computer or server. The remote computer may be connected to the user's computer through any type of network, including, for example, a local area network (LAN) or a wide area network (WAN), or the connection may be made to an external computer (for example, through the Internet using an Internet Service Provider).

Figure 2:
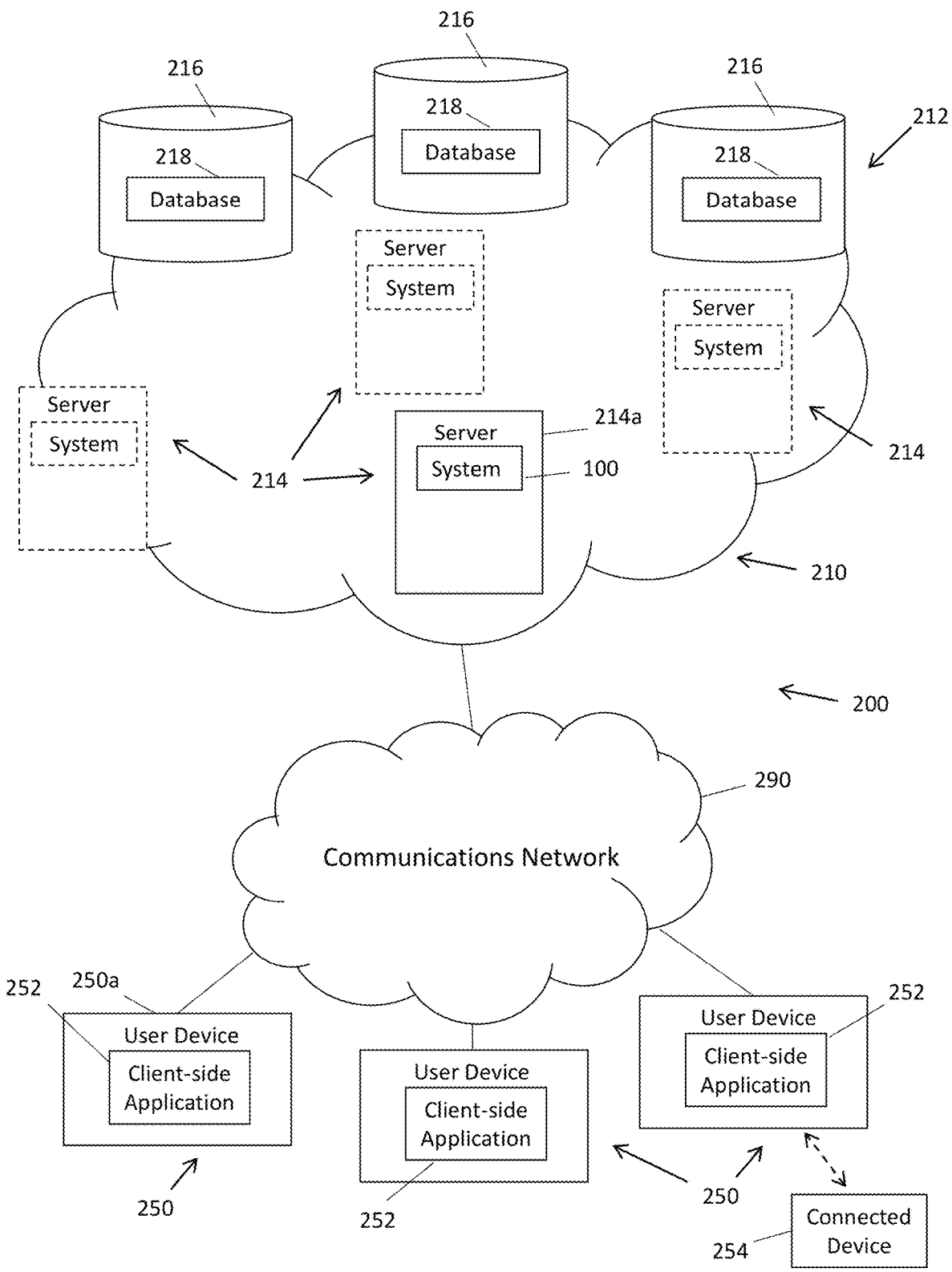
FIG. 2 depicts an example computing environment for implementing embodiments of the system in accordance with embodiments of the present disclosure.
Figure 3:
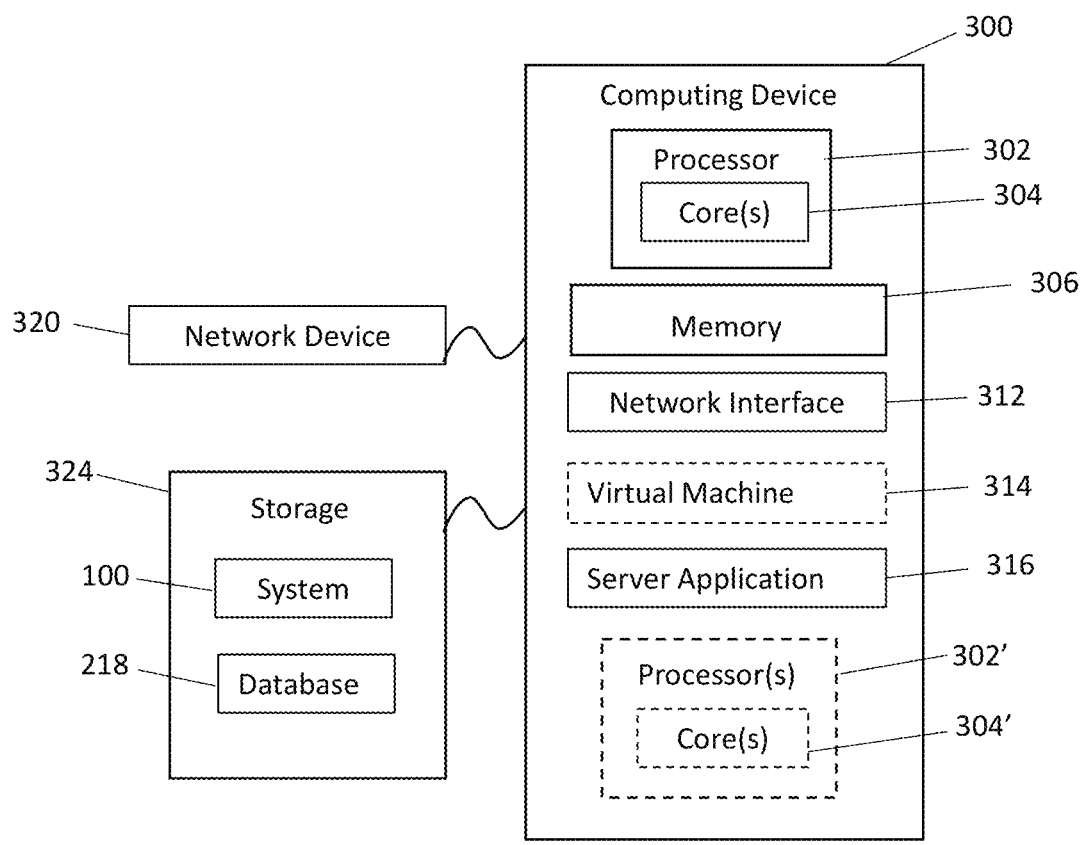
FIG. 3 is a block diagram of an exemplary computing device for implementing one or more of the servers in accordance with embodiments of the present disclosure.

FIG. 2 depicts an example computing environment for implementing embodiments of the system 100 in accordance with embodiments of the present disclosure. As shown in FIG. 2, the environment 200 can include distributed computing system 210 including shared computer resources 212, such as servers 214 and (durable) data storage devices 216, which can be operatively coupled to each other. For example, two or more of the shared computer resources 212 can be directly connected to each other or can be connected to each other through one or more other network devices, such as switches, routers, hubs, and the like. Each of the servers 214 can include at least one processing device (e.g., a central processing unit, a graphical processing unit, etc.) and each of the data storage devices 216 can include non-volatile memory for storing databases 218. The databases 218 can store data 220 including, for example, embodiments of the composite image database 102, the elemental image database 104, and/or the image vignette database 106. An exemplary server is depicted in FIG. 3.

Any one of the servers 214 can implement instances of the system 100 and/or the components thereof. In some embodiments, one or more of the servers 214 can be a dedicated computer resource for implementing the system 100 and/or components thereof. In some embodiments, one or more of the servers 214 can be dynamically grouped to collectively implement embodiments of the system 100 and/or components thereof. In some embodiments, one or more servers can dynamically implement different instances of the system 100 and/or components thereof.

Figure 4:
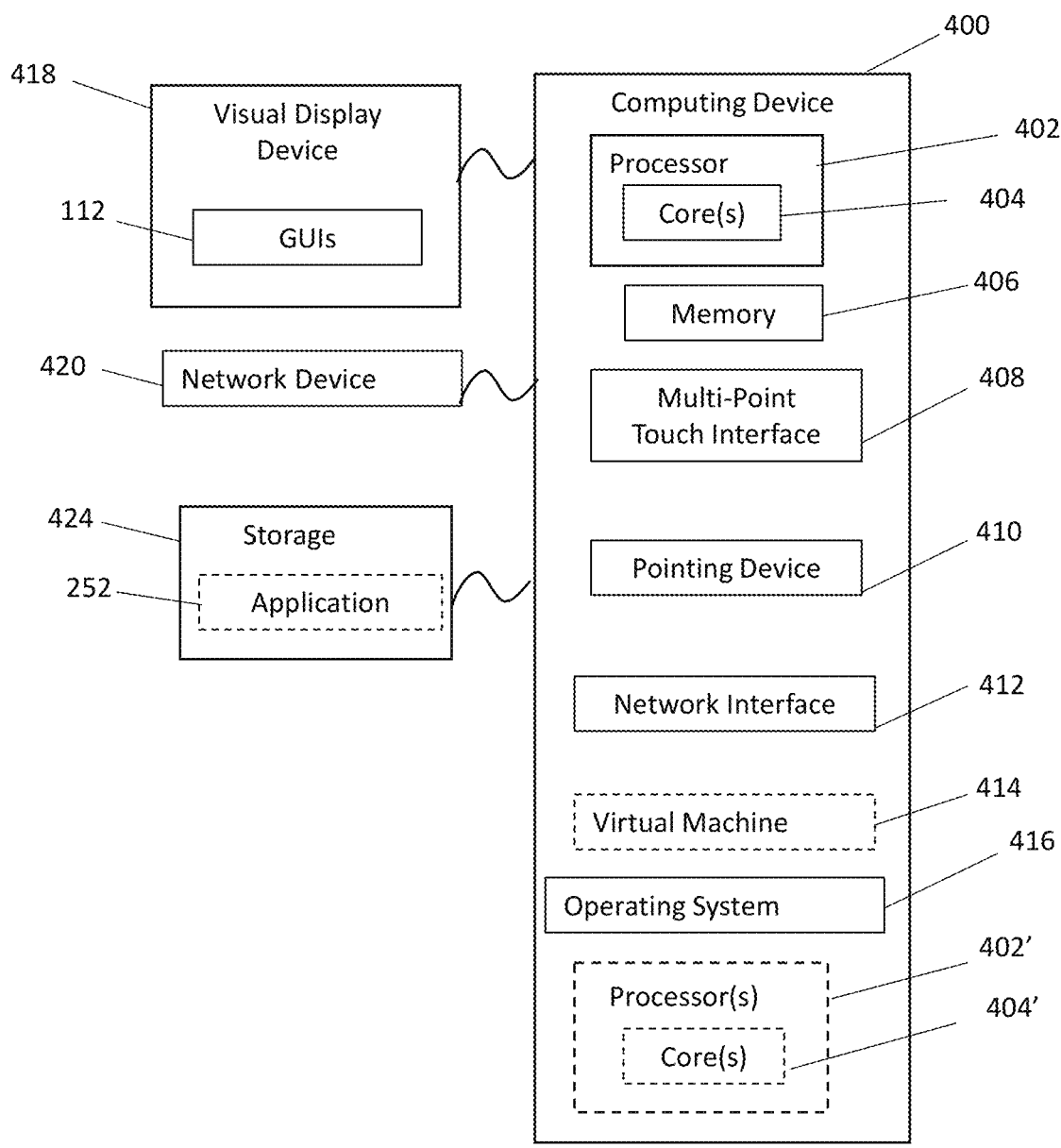
FIG. 4 is a block diagram of an exemplary computing device for implementing one or more of the client devices in accordance with embodiments of the present disclosure.

The distributed computing system 210 can facilitate a multi-user, multi-tenant environment that can be accessed concurrently and/or asynchronously by client devices 250. For example, the client devices 250 can be operatively coupled to one or more of the servers 214 and/or the data storage devices 216 via a communication network 290, which can be the Internet, a wide area network (WAN), local area network (LAN), and/or other suitable communication network. The client devices 250 can execute client-side applications 252 to access the distributed computing system 210 via the communications network 290. The client-side application(s) 252 can include, for example, a web browser and/or a specific application for accessing and interacting with the system 100. In some embodiments, the client side application(s) 252 can be a component of the system 100 that is downloaded and installed on the client devices (e.g., an application, such as a mobile application). An exemplary client device is depicted in FIG. 4.

In exemplary embodiments, the client devices 250 can initiate communication with the distributed computing system 210 via the client-side applications 252 to establish communication sessions with the distributed computing system 210 that allows each of the client devices 250 to utilize the system 100, as described herein. For example, in response to the client device 250a accessing the distributed computing system 210, the server 214a can launch an instance of the system 100. In some embodiments, the client device 20 can be connected to connected device 254, such as wearable device including smart watches, heartrate monitors, and/or fitness trackers, which can provide information to the system 100 via the client device as described herein. In embodiments which utilize multi-tenancy, if an instance of the system 100 has already been launched, the instance of the system 100 can process multiple users simultaneously. The server 214a can execute instances of each of the components of the system 100 according to embodiments described herein. Upon being launched, the system 100 can identify the current state of the data associated with the user that is stored in the databases in data storage locations of one or more of the data storage devices 216. For example, the server 214a can generate and/or load image vignettes corresponding to a specific user accessing the system 100.

FIG. 3 is a block diagram of an exemplary computing device 300 for implementing one or more of the servers 214 in accordance with embodiments of the present disclosure. In the present embodiment, the computing device 300 is configured as a server that is programmed and/or configured to execute one of more of the operations and/or functions for embodiments of the system 100 and to facilitate communication with the client devices described herein (e.g., client device(s) 250). The computing device 300 includes one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, one or more optical disks, one or more solid state drives), and the like. For example, memory 306 included in the computing device 300 can store computer-readable and computer-executable instructions or software for implementing exemplary embodiments of the components/modules of the system 100 or portions thereof, for example, by the servers 214. The computing device 300 also includes configurable and/or programmable processor 302 and associated core 304, and optionally, one or more additional configurable and/or programmable processor(s) 302' (e.g., central processing unit, graphical processing unit, etc.) and associated core(s) 304' (for example, in the case of computer systems having multiple processors/cores), for executing computer-readable and computer-executable instructions or software stored in the memory 306 and other programs for controlling system hardware. Processor 302 and processor(s) 302' may each be a single core processor or multiple core (304 and 304') processor.

Virtualization may be employed in the computing device 300 so that infrastructure and resources in the computing device may be shared dynamically. One or more virtual machines 314 may be provided to handle a process running on multiple processors so that the process appears to be using only one computing resource rather than multiple computing resources. Multiple virtual machines may also be used with one processor.

Memory 306 may include a computer system memory or random access memory, such as DRAM, SRAM, EDO RAM, and the like. Memory 306 may include other types of memory as well, or combinations thereof.

The computing device 300 may include or be operatively coupled to one or more data storage devices 324, such as a hard-drive, CD-ROM, mass storage flash drive, or other computer readable media, for storing data and computer-readable instructions and/or software that can be executed by the processing device 302 to implement exemplary embodiments of the components/modules described herein with reference to the servers 214.

The computing device 300 can include a network interface 312 configured to interface via one or more network devices 320 with one or more networks, for example, a Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections (including via cellular base stations), controller area network (CAN), or some combination of any or all of the above. The network interface 312 may include a built-in network adapter, network interface card, PCMCIA network card, card bus network adapter, wireless network adapter, USB network adapter, modem or any other device suitable for interfacing the computing device 300 to any type of network capable of communication and performing the operations described herein. While the computing device 300 depicted in FIG. 3 is implemented as a server, exemplary embodiments of the computing device 300 can be any computer system, such as a workstation, desktop computer or other form of computing or telecommunications device that is capable of communication with other devices either by wireless communication or wired communication and that has sufficient processor power and memory capacity to perform the operations described herein.

The computing device 300 may run any server operating system or application 316, such as any of the versions of server applications including any Unix-based server applications, Linux-based server application, any proprietary server applications, or any other server applications capable of running on the computing device 300 and performing the operations described herein. An example of a server application that can run on the computing device includes the Apache server application.

FIG. 4 is a block diagram of an exemplary computing device 400 for implementing one or more of the client devices (e.g., client devices 250) in accordance with embodiments of the present disclosure. In the present embodiment, the computing device 400 is configured as a client-side device that is programmed and/or configured to execute one of more of the operations and/or functions for embodiments of the client-side applications 252 and to facilitate communication with the servers described herein (e.g., servers 214). The computing device 400 includes one or more non-transitory computer-readable media for storing one or more computer-executable instructions or software for implementing exemplary embodiments of the application described herein (e.g., embodiments of the client-side applications 252, the system 100, or components thereof). The non-transitory computer-readable media may include, but are not limited to, one or more types of hardware memory, non-transitory tangible media (for example, one or more magnetic storage disks, one or more optical disks, one or more solid state drives), and the like. For example, memory 406 included in the computing device 400 may store computer-readable and computer-executable instructions, code or software for implementing exemplary embodiments of the client-side applications 252 or portions thereof. In some embodiments, the client-side applications 252 can include one or more components of the system 100 such that the system is distributed between the client devices and the servers 214. For example, the client-side application can include the visual editor 150. In some embodiments, the client-side application can interface with the system 100, where the components of the system 100 reside on and are executed by the servers 214.

The computing device 400 also includes configurable and/or programmable processor 402 (e.g., central processing unit, graphical processing unit, etc.) and associated core 404, and optionally, one or more additional configurable and/or programmable processor(s) 402' and associated core(s) 404' (for example, in the case of computer systems having multiple processors/cores), for executing computer-readable and computer-executable instructions, code, or software stored in the memory 406 and other programs for controlling system hardware. Processor 402 and processor(s) 402' may each be a single core processor or multiple core (404 and 404') processor.

Virtualization may be employed in the computing device 400 so that infrastructure and resources in the computing device may be shared dynamically. A virtual machine 414 may be provided to handle a process running on multiple processors so that the process appears to be using only one computing resource rather than multiple computing resources. Multiple virtual machines may also be used with one processor.

Memory 406 may include a computer system memory or random access memory, such as DRAM, SRAM, MRAM, EDO RAM, and the like. Memory 406 may include other types of memory as well, or combinations thereof.

A user may interact with the computing device 400 through a visual display device 418, such as a computer monitor, which may be operatively coupled, indirectly or directly, to the computing device 400 to display one or more of graphical user interfaces of the system 100 that can be provided by or accessed through the client-side applications 252 in accordance with exemplary embodiments. The computing device 400 may include other I/O devices for receiving input from a user, for example, a keyboard or any suitable multi-point touch interface 408, and a pointing device 410 (e.g., a mouse). The keyboard 408 and the pointing device 410 may be coupled to the visual display device 418. The computing device 400 may include other suitable I/O peripherals.

The computing device 400 may also include or be operatively coupled to one or more storage devices 424, such as a hard-drive, CD-ROM, or other computer readable media, for storing data and computer-readable instructions, executable code and/or software that implement exemplary embodiments of the client-side applications 252 and the system 100 or portions thereof as well as associated processes described herein.

The computing device 400 can include a network interface 412 configured to interface via one or more network devices 420 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 412 may include a built-in network adapter, network interface card, PCMCIA network card, card bus network adapter, wireless network adapter, USB network adapter, modem or any other device suitable for interfacing the computing device 400 to any type of network capable of communication and performing the operations described herein. Moreover, the computing device 400 may be any computer system, such as a workstation, desktop computer, server, laptop, handheld computer, tablet computer (e.g., the iPad™ tablet computer), mobile computing or communication device (e.g., a smart phone, such as the iPhone™ communication device or Android communication device), wearable devices (e.g., smart watches), internal corporate devices, or other form of computing or telecommunications device that is capable of communication and that has sufficient processor power and memory capacity to perform the processes and/or operations described herein.

The computing device 400 may run any operating system 416, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, or any other operating system capable of running on the computing device and performing the processes and/or operations described herein. In exemplary embodiments, the operating system 416 may be run in native mode or emulated mode. In an exemplary embodiment, the operating system 416 may be run on one or more cloud machine instances.

Figure 5:
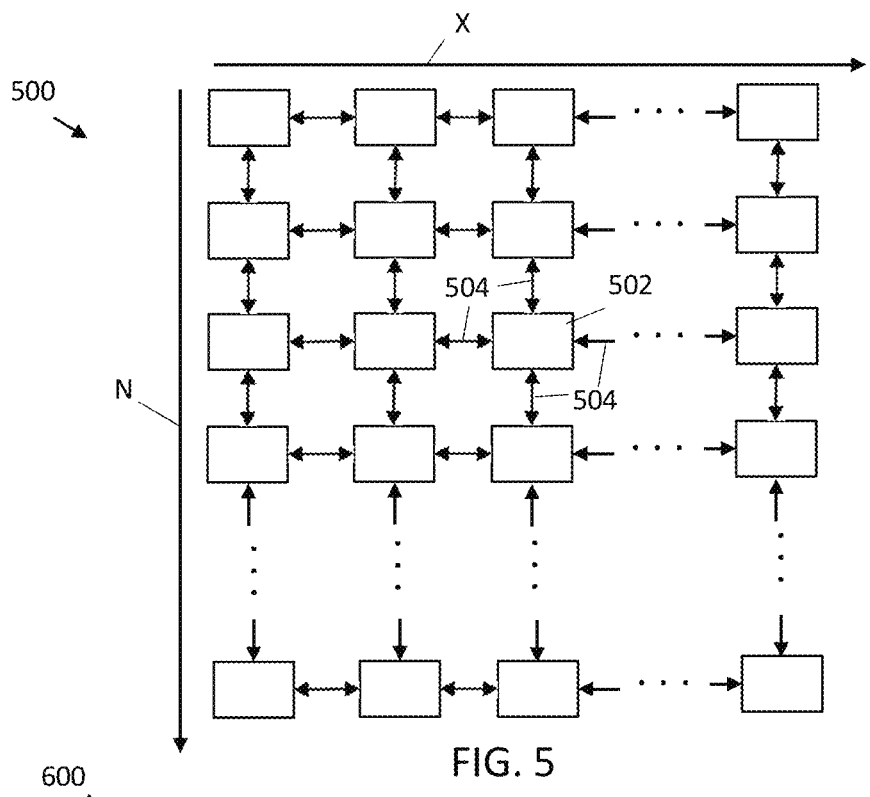
FIG. 5 illustrates an example image-based database structure for composite images or image vignettes utilized in embodiments of the present disclosure.

FIG. 5 illustrates an example image-based database structure 500 for composite images and/or image vignettes utilized in embodiments of the system 100. The image-based database structure can include a map or grid defined by a coordinate system based on a type parameter N and a quality level parameter X assigned to each record in the database. The direction of the arrow associated with the type parameter N illustrates an moving within the grid from a worst or lowest type to a best or highest type. Likewise, the direction of the arrow associated with the quality type parameter X illustrates an moving within the grid from a worst or lowest quality level to a best or highest quality level. Each record 502 in the grid can be linked or point 504 to its nearest neighbors in both the type and the quality level to create the grid or map. As one example, a record associated with a first composite image or image vignette having a specified level X and type N can be linked with or point to records of a composite image having the same type N, but with level X that is incremented and/or decremented by one. As another example, a record associated with a first composite image having a specified level X and type N can be linked with or point to records of a composite image having the same level X, but with a type N that is incremented and/or decremented by one. Employing this grid-based architecture in the composite image database 102, advantageously allows the system 100 to identify not only a record of a specific composite image based on a query that includes a specified level X and a specified type N, but also allows the system to identify those records for additional composite images that are considered the nearest neighbor of the specific composite image. This can allow the system 100 to retrieve additional composite images without executing a query for the additional composite images (e.g., by retrieving images around the composite image in the map or grid). The structure of the composite image database 102 therefore allows the system 100 to not only pin point a specific composite image but to also target an area in the grid or map corresponding to a group of linked composite images associated with a diet type and/or a diet quality level.

Figure 6:
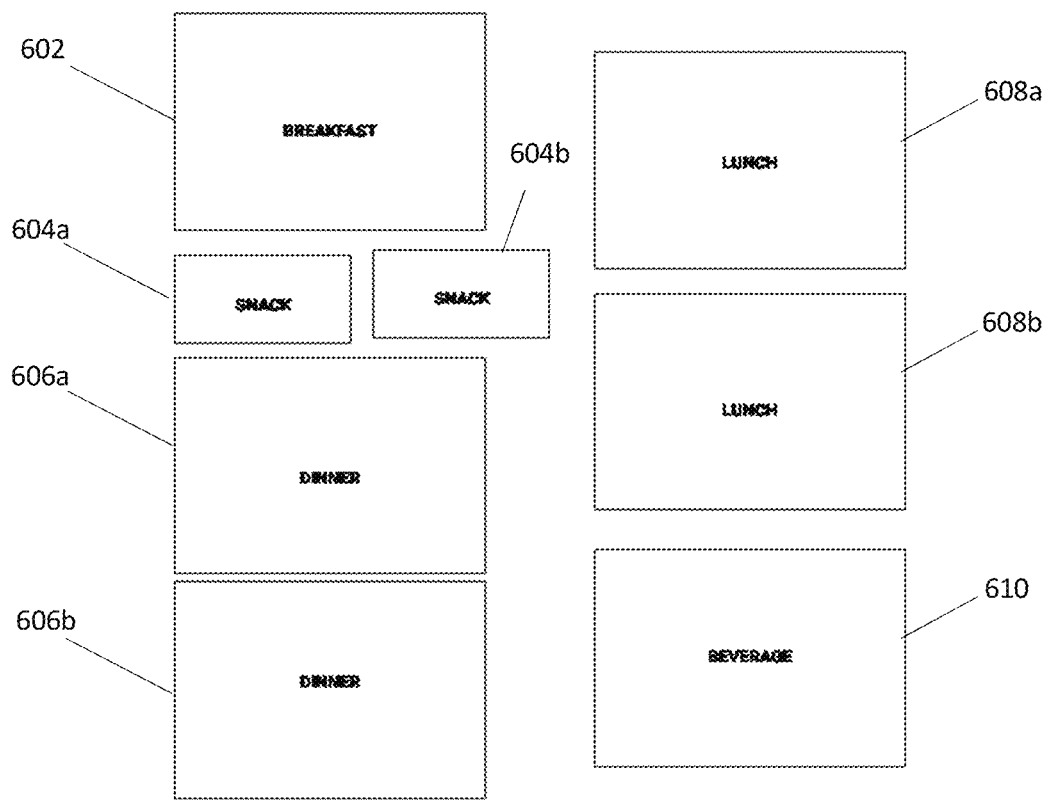
FIG. 6 illustrates an example image-based database structure for elemental images utilized in embodiments of the present disclosure.

FIG. 6 illustrates a composition of an example image vignette 600 in accordance with embodiments of the present disclosure. As shown in FIG. 6, the image vignette 600 can be structured to define areas 602-610 that specify locations or slots at which elements for elemental images or elements from composite imaged can be incorporated into the image canvas of the image vignette. For example, the area 602 defines a location or slot at which an element corresponding to a breakfast dish can be inserted, the areas 604a-b define a location or slot at which elements corresponding to snacks can be inserted, the areas 606a-b define a location or slot at which elements corresponding to dinners can be inserted, the areas 608a-b define a location or slot at which elements corresponding to lunches can be inserted, and the area 610 defines a location or slot at which an element corresponding to a beverage can be inserted.

Figure 7:
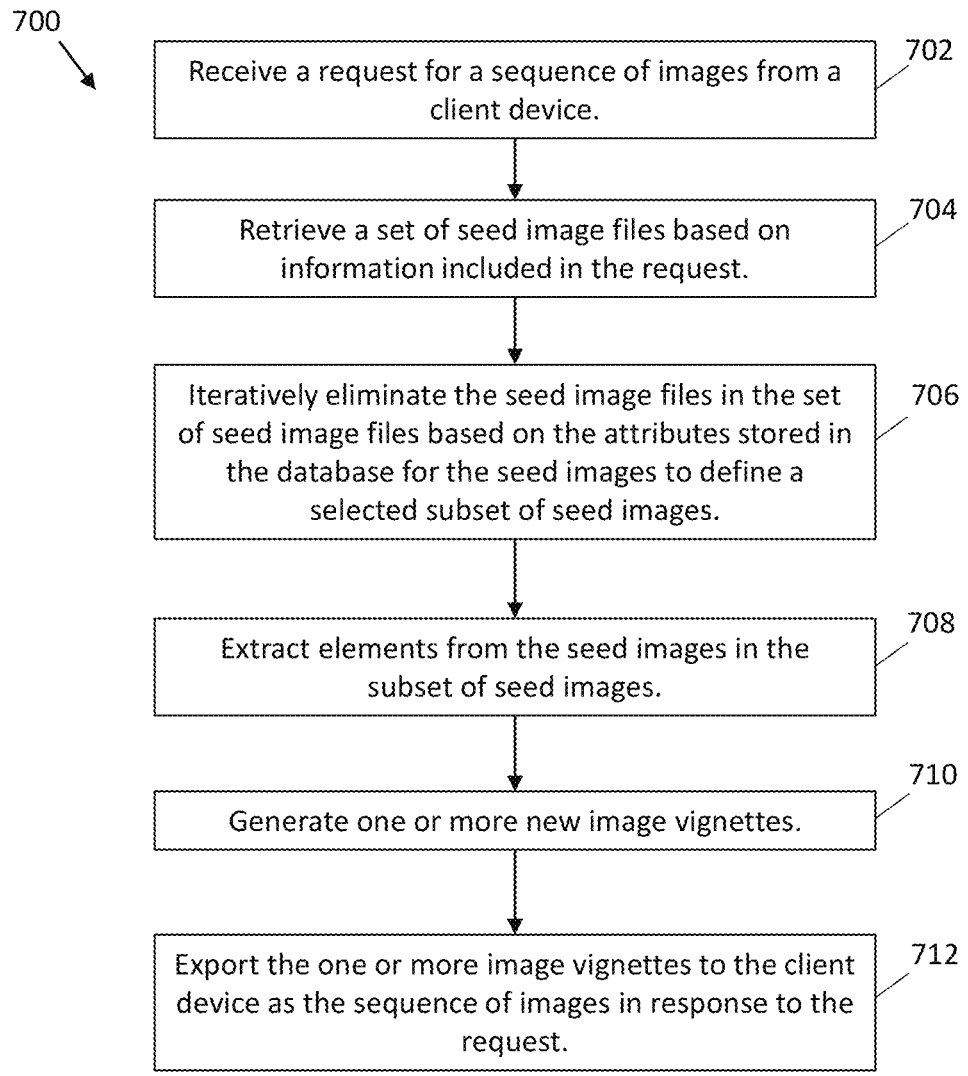
FIG. 7 is a flowchart illustrating an example process for generating image vignettes in accordance with embodiments of the present disclosure.

FIG. 7 is a flowchart illustrating an example process 700 for generating image vignettes in accordance with embodiments of the present disclosure. At operation 702, a request for a sequence of images from a client device can be received at a server. At operation 704, a database (e.g., the database 102 or 104) including a plurality of records including seed images and attributes associated with content depicted in the seed images can be queried by the server to retrieve a set of seed image files based on information included in the request. The content of the seed images can include a least one of food or beverages. Each seed image can be assigned a diet type and a diet quality level based on the attributes associated with the content of the seed images. In exemplary embodiments, the seed images can be the composite images or the elemental images. At operation 706, the seed image files in the set of seed image files can be iteratively eliminated by the server, based on the attributes stored in the database for the seed images, to define a selected subset of seed images. At operation 708, elements from the seed images in the subset of seed images can be extracted via the server, and at operation 710, one or more new image vignettes can be generated by the server based on the extracted elements from the subset of seed images. Each new image vignette can incorporate at least two of the elements extracted from the seed images in the subset of seed images. At operation 712, the one or more image vignettes can be exported via the server to the client device as the sequence of images in response to the request. In exemplary embodiments, the server can determine one or more properties associated with the client device (e.g., based on the request or any suitable technique) and a quantity of image vignettes that the server generates and exports can depend at least in part on a property associated with the client device. The property of the client device can be, for example, at least one of a size of a display of the client device, an available memory capacity of the client device, or a network connection speed at which the client device is operating. As an example, more image vignettes can be generated and exported to the client device upon determining that the client device has a larger display, more memory capacity, and/or a higher network connection speed. As another example, fewer image vignettes can be generated and exported to the client device upon determining that the client device has a smaller display, less memory capacity, and/or a lower network connection speed.

In some embodiments, a temporary memory location can be allocated for storing the one or more image vignettes, instances of the one or more image vignettes can be stored in the temporary memory, and/or the instances of the one or more image vignettes can be deleted from the temporary memory by the server to deallocate the temporary memory location after the one or more image vignettes are exported.

In some embodiments, the one or more seed images can be at least one of a composite image depicts a unique inventory of proportions of foods, ingredients, dishes and meals representative of a particular diet quality level X of a particular diet type N for a period of time or an elemental images of integrated unit of foods or a beverage.

Figure 8:
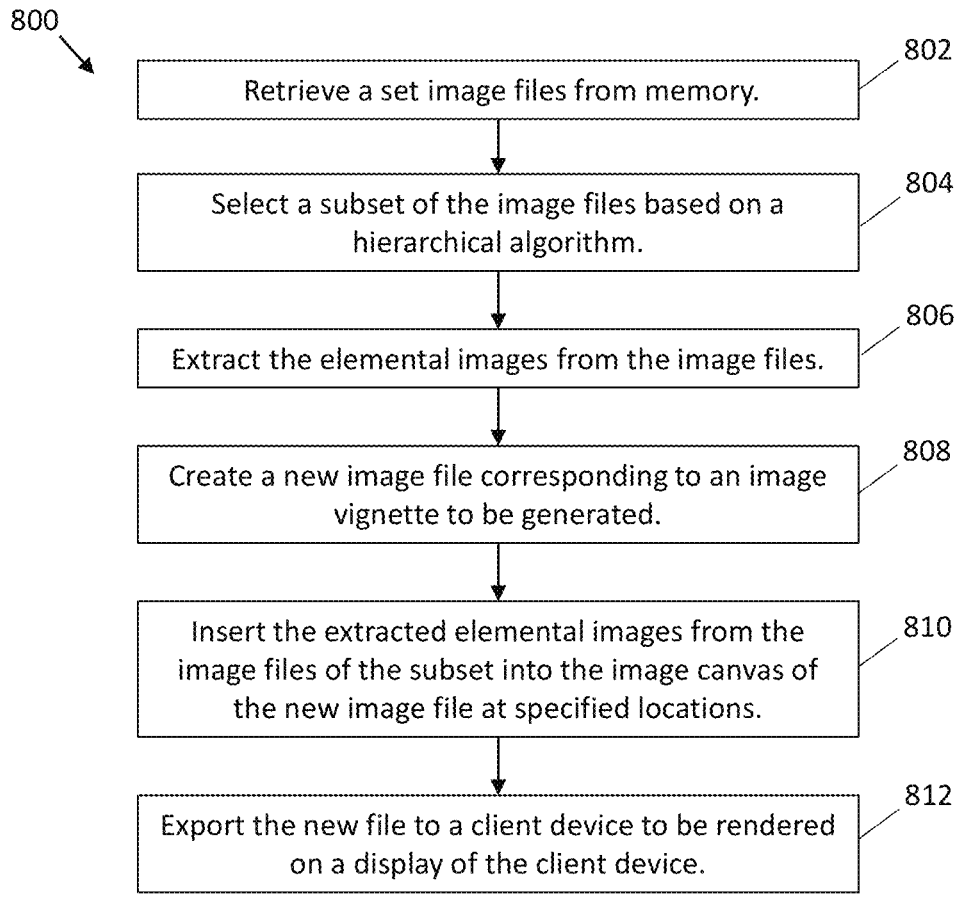
FIG. 8 is a flowchart illustrating an example process for generating image vignettes from elemental images in accordance with embodiments of the present disclosure.

FIG. 8 is a flowchart illustrating an example process 800 for generating image vignettes from elemental images in accordance with embodiments of the present disclosure. As described herein, an elemental image database can be created that includes elemental images and tags representing data or information corresponding to attributes or characteristics of the content represented by the elemental images. At operation 802, one or more processors executing an embodiment of the system 100 can query the elemental images database to retrieve a set image files from memory corresponding to elemental images based on the tags in the elemental image database. As an example, embodiments of the system 100 can generate one or more queries for elemental images having tags that correspond to one or more specified dietary patterns. In some embodiments, the one or more processors can receive a request for a sequence of images from a client device and can generate the image vignettes in response to the request. In some embodiments, the one or more processors can pre-generate the image vignettes for each diet type and diet quality level provided by the system 100.

At operation 804, the one or more processors executing an embodiment of the system 100 select a subset of the image files based on a hierarchical algorithm that receives as an input the tags associated with the elemental images. As an example, the one or more processors can execute the hierarchical algorithm to iteratively eliminate image files from the set of retrieved image files based on the tags associated with the elemental images associated with the image files as described herein, e.g., with reference to FIG. 9.

At operation 806, the one or more processors executing an embodiment of the system 100 can extract the elemental images from the image files associated with the subset of the selected elemental images. At operation 808, the one or more processors executing an embodiment of the system 100 create a new image file corresponding to an image vignette to be generated based on the selected elemental images, where the new image file defines an image canvas. At operation 810, the one or more processors executing an embodiment of the system 100 can inserting the extracted elemental images from the image files of the subset into the image canvas of the new image file at specified locations. At operation 812, the one or more processors executing an embodiment of the system can export the new file to a client device to be rendered on a display of the client device.

Figure 9:
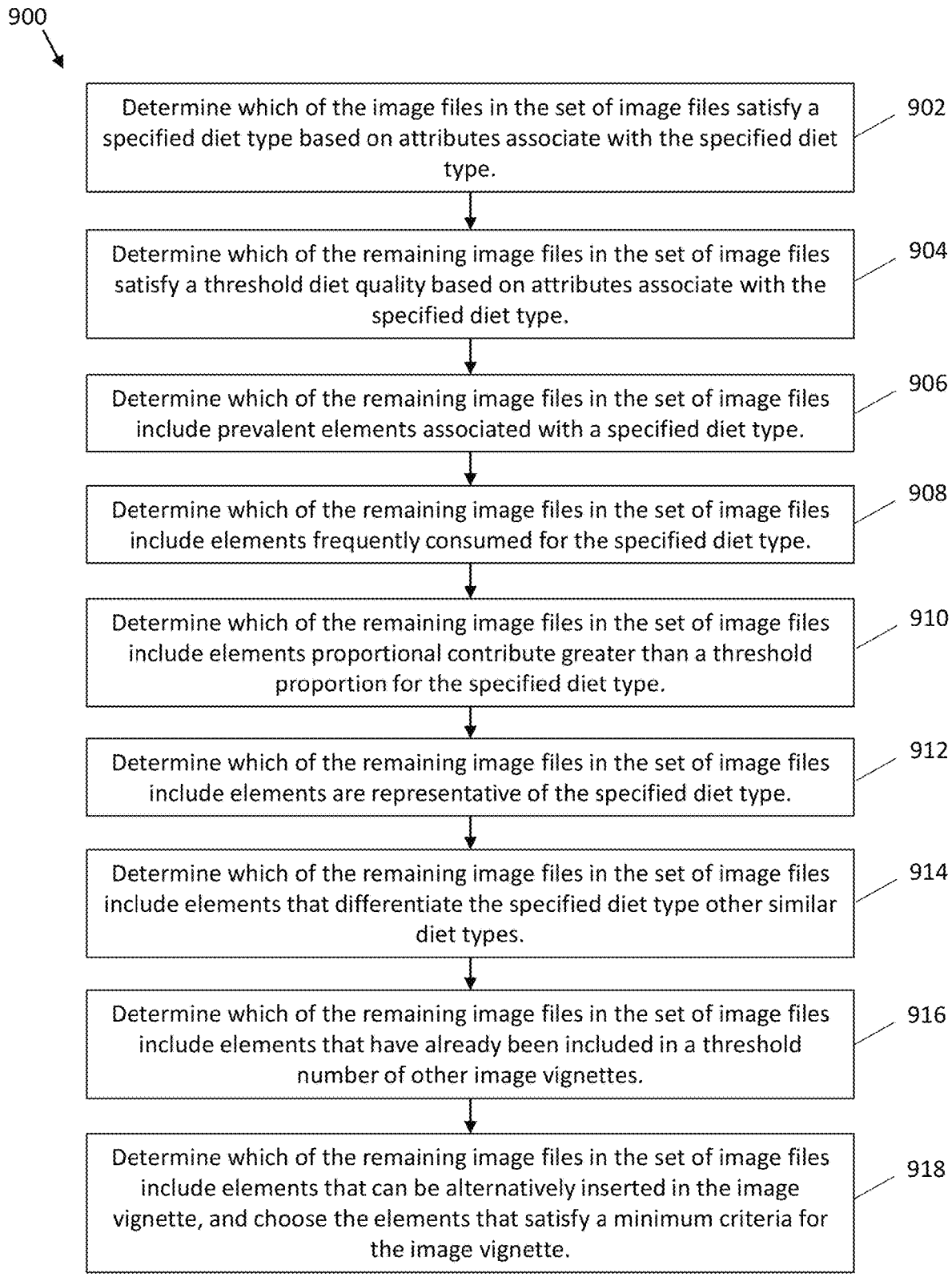
FIG. 9 is a flowchart illustrating an example process of a hierarchical algorithm for selecting a subset of image files corresponding to elemental images from a set of image files to be used to generate a new image file corresponding to an image vignette in accordance with embodiments of the present disclosure.

FIG. 9 is a flowchart illustrating an example process 900 for a hierarchical algorithm for selecting a subset of image files corresponding to elemental images from a set of image files retrieved in response to querying the elemental image database to be used for generating a new image file corresponding to an image vignette. At operation 902, one or more processors executing an embodiment of the system 100 can determine which of the image files in the set of image files satisfy a specified diet type based on attributes associate with the specified diet type. Image files in the set that do not satisfy the specified diet type can be eliminated from the set of image files. At operation 904, the one or more processors executing an embodiment of the system 100 can determine which of the remaining image files in the set of image files satisfy a threshold diet quality based on attributes associate with the specified diet type. Image files in the set that do not satisfy the threshold diet quality can be eliminated from the set of image files. At operation 906, the one or more processors executing an embodiment of the system 100 can determine which of the remaining image files in the set of image files include prevalent elements associated with a specified diet type. Image files in the set that do not prevalent elements associated with the specified diet quality can be eliminated from the set of image files. At operation 908, the one or more processors executing an embodiment of the system 100 can determine which of the remaining image files in the set of image files include elements frequently consumed for the specified diet type. Images files in the set that do not satisfy a specified frequency threshold can be eliminated from the set. At operation 910, the one or more processors executing an embodiment of the system 100 can determine which of the remaining image files in the set of image files include elements proportional contribute greater than a threshold proportion for the specified diet type. Images files in the set that do not satisfy the threshold proportion can be eliminated from the set.

At operation 912, the one or more processors executing an embodiment of the system 100 can determine which of the remaining image files in the set of image files include elements are representative of the specified diet type. Images files in the set that are determine not to be representative of the specified diet type can be eliminated from the set. At operation 914, the one or more processors executing an embodiment of the system 100 can determine which of the remaining image files in the set of image files include elements that differentiate the specified diet type other similar diet types. Images files in the set that do not satisfy a specified exclusivity threshold can be eliminated from the set. At operation 916, the one or more processors executing an embodiment of the system 100 can determine which of the remaining image files in the set of image files include elements that have already been included in a threshold number of other image vignettes. Images files in the set that have been included in threshold number of other image vignettes can be eliminated from the set. At operation 918, the one or more processors executing an embodiment of the system 100 can determine which of the remaining image files in the set of image files include elements that can be alternatively inserted in the image vignette, and can choose the elements that satisfy a minimum criteria for the image vignette, and eliminate the remaining image files. The elements in the elemental images of the remaining subset of image files can be used to generate the image vignette.

Figure 10:
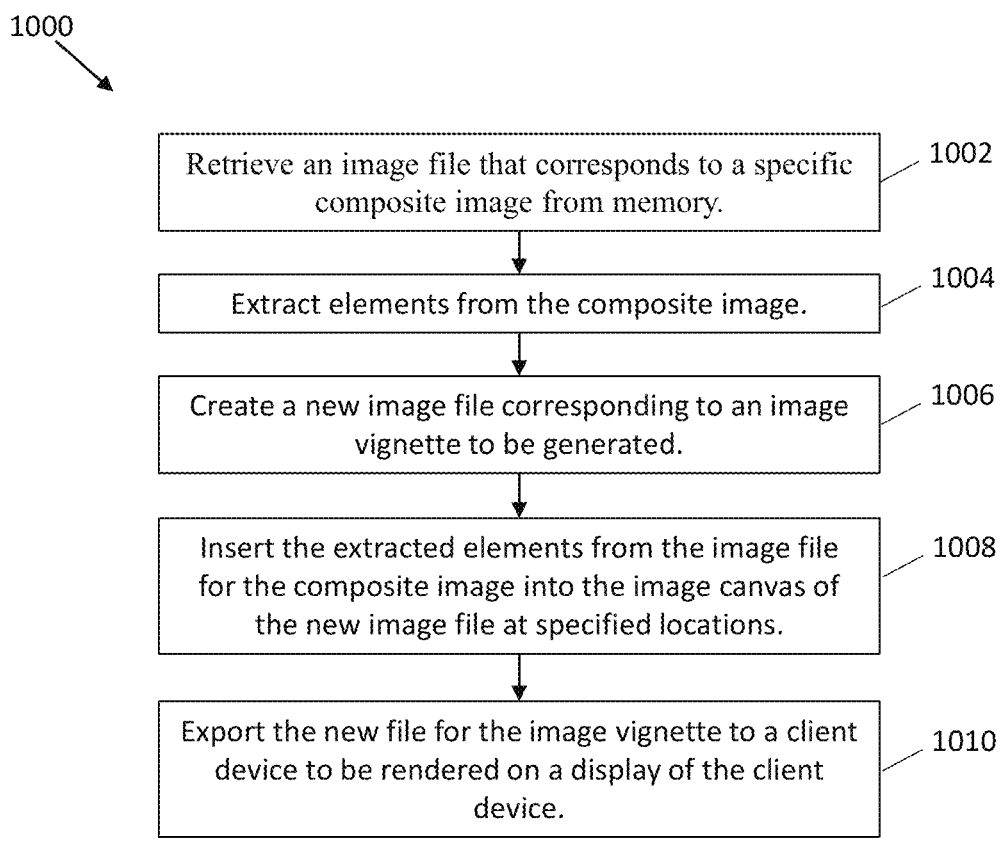
FIG. 10 is a flowchart illustrating an example process for generating image vignettes from composite images in accordance with embodiments of the present disclosure.

FIG. 10 is a flowchart illustrating an example process 1000 for generating image vignettes from composite images in accordance with embodiments of the present disclosure. As described herein, a database of composite images can be created that includes tags that define coordinates of the composite image in a grid of composite images. At operation 1002, one or more processors executing an embodiment of the system 100 can query the database of composite images and retrieve an image file that corresponds to a specific composite image from memory based on the tags in the database. As an example, the query can include the coordinates of the specific composite image in the grid. At operation 1004, the one or more processors executing an embodiment of the system 100 can perform one or more imaging processing and/or machine vision to process the composite images and extract element from the composite images. For example, the one or more processors executing the system can use Stitching/Registration, Filtering. Thresholding, Pixel counting, Segmentation, Inpainting, Edge detection, Color Analysis, Blob discovery and manipulation, Neural net processing, Pattern recognition, Optical character recognition, blurring, normalized lighting, greyscaling, OTSU, thresholding, erosion/dilation, convert correct hull, contour detection, blob/mass calculation normalization, and/or Gauging/Metrology to extract elements from the composite image based on, for example, the hierarchical algorithm described with reference to FIG. 9. At operation 1006, the one or more processors executing an embodiment of the system create a new image file corresponding to an image vignette to be generated based on the extracted elements, where the new image file defines an image canvas. At operation 1008, the one or more processors executing an embodiment of the system 100 can inserting the extracted elements from the image file for the composite image into the image canvas of the new image file at specified locations. At operation 1010, the one or more processors executing an embodiment of the system 100 can export the new file for the image vignette to a client device to be rendered on a display of the client device.

Figure 11:
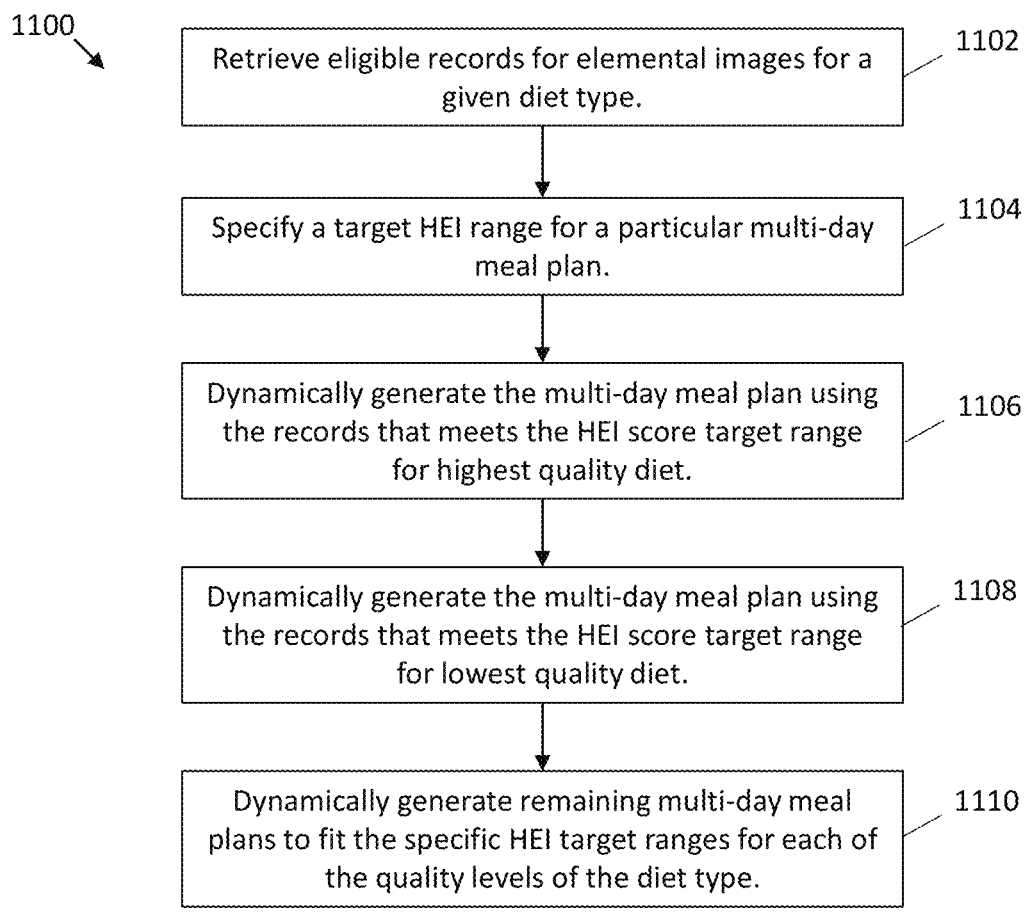
FIG. 11 is a flowchart illustrating an example process of embodiments of the present disclosure.

FIG. 11 is a flowchart illustrating an example process 1000 of embodiments of embodiments of the present disclosure. At operation 1102, all eligible records for elemental images for a given diet type are retrieved from the elemental database by one or more processors based on their associated defining attribute by type (DAT) attribute(s). Each record can include a dish or beverage name, food group information, ingredient information, relevant attribute tags such as dietary restrictions and meal type (e.g. breakfast, snack), defining attributes by quality level (DAQ) inclusion and exclusions, and corresponding elemental image. For example, all eligible records for a given diet type can include hundreds records of food and dishes that can be consumed at any quality level within a particular style of eating. The attributes associate with a specific dietary pattern can be used to narrow the returned records to a subset of records, for example, based on the specific diet type's DATs, the specific diet type's DAQs, a prevalence of entry types (e.g. an association between geography, culture and common food items associated with the same). The one or more processors executing an embodiment of the system can perform the hierarchical algorithm or a portion thereof described with respect to FIG. 9 to identify a subset of records that can be used to generate the image vignette. The one or more processors executing an embodiment of the system 100 can dynamically assemble a multi-day meal plan based on eligible records in the subset. The multi-day meal plan can include the dish/beverage entries, the total nutrients for the day, and the total food groups per day. The one or more processors perform a real-time calculation of the Healthy Eating Index score for the multi-day meal plan using the standard Healthy Eating Index calculation algorithm. At operation 1104, a target HEI range for a particular multi-day meal plan is specified. At operation 1106, the one or more processors dynamically generate the highest quality multi-day meal plan using the eligible food/dish records, such that each day's meal plan contains a breakfast, lunch, dinner, 1+ beverage, and 1+ snack, such that the assembled meal plan meets the DAQs and the meal plan meets the HEI score target range. At operation 1108, the one or more processors dynamically generate the lowest quality multi-day meal plan using the eligible food/dish records, such that each day's meal plan contains a breakfast, lunch, dinner, 1+ beverage, and 1+ snack, such that the assembled meal plan meets the DAQs and the meal plan meets the HEI score target range. At operation 1110, the one or more processors that dynamically generate remaining multi-day meal plans to fit the specific HEI target range for each "cell" in the diet type column. For example, if a diet type is to have 10 tiers or quality levels, the one or more processors executing an embodiment of the system 100 can dynamically generate a total of 10 multi-day meal plans to meet the specifications of each tier or cell. As an example, embodiments of the system 100 can start by assembling tier 10, followed by assembling tier 1, which set the upper and lower bounds, and then can dynamically generate tier 2, 3, 4, 5, 6, 7, and 8. Each tier has a target HEI score range, so the dynamically assembled multi-day meal plan score falls in that HEI score range. Once the meal plans are established, the elements in the elemental images associated with the meal plans are extracted and inserted into new image files for image vignettes for each tier or quality level.

Figure 12:
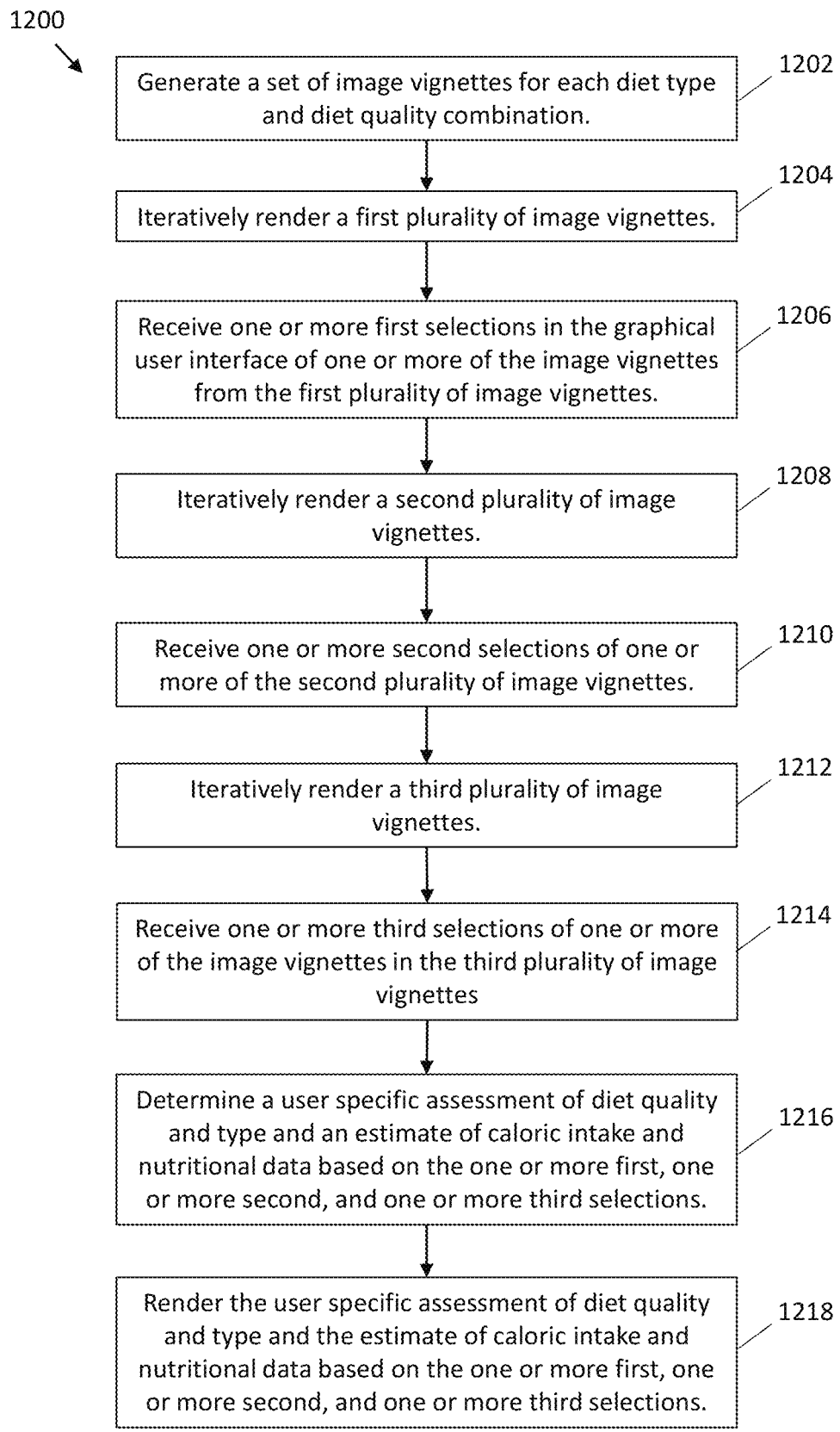
FIG. 12 is a flowchart illustrating an example process of embodiments of the present disclosure.

FIG. 12 is a flowchart illustrating an example process 1200 of embodiments of the system 100 executed by one or more processors in response to user interaction via a graphical user interface in accordance with embodiments of the present disclosure. At operation 1202, a set of image vignettes for each diet type and diet quality combination can be generated by one or more processors. At operation 1204, a first plurality of image vignettes can be iteratively rendered in a graphical user interface for selection by a user. Each of the image vignettes presents dietary characteristics of at least one of a different diet quality level or a different diet type. At operation 1206, one or more first selections in the graphical user interface of one or more of the image vignettes from the first plurality of image vignettes can be received from the user. The iterative rendering of image vignettes in the first plurality of images and receiving selections for each iteration can be used to narrow down particularly area within the grid or map from which additional pluralities of image vignettes can be rendered to assess the diet type and diet quality of the user. At operation 1208, in response to receipt of the first selection in the graphical user interface, a second plurality of image vignettes can be iteratively rendered in the graphical user interface for selection by the user. The one or more processors can choose the second plurality of image vignettes to be rendered based on the first selection by the user such that the second plurality of image vignettes chosen by the one or more processors depends on the one or more first selections. The second plurality of image vignettes can include at least one image vignette that is different from the image vignettes in the first plurality of image vignettes. At operation 1210, one or more second selections of one or more of the second plurality of image vignettes in the graphical user interface can be received from the user. At operation 1212, in response to receiving the one or more second selections in the graphical user interface, a third plurality of image vignettes can be iteratively rendered in the graphical user interface for selection by the user. At least one of image vignettes in the third plurality of image vignettes is different from the second plurality of images vignettes. At operation 1214, one or more third selections of one or more of the image vignettes in the third plurality of image vignettes in the graphical user interface can be received from the user. At operation 1216, a user specific assessment of diet quality and type and an estimate of caloric intake and nutritional data can be determined for the user based on the one or more first, one or more second, and one or more third selections. The one or more first selections can used to determine a diet type of the user and the one or more second and one or more third selections can be used to determine a diet quality level of the user. The iterative rendering of image vignettes from the first, second, and third plurality of images and receipt selections for each iteration can be used to assess the diet type and diet quality of the user. For example, with each selection, the system 100 can move closer to a diet type or quality level for the user until the system 100 converges on the diet type and quality level for the user. After each selection by the user of a derivative image vignette, the system 100 determines the next several derivative image vignettes to display and this is repeated multiple times. In one embodiment, the number of derivative images displayed on each scroll bar can be two or more. At operation 1218, the user specific assessment of diet quality and type and the estimate of caloric intake and nutritional data can be rendered in the graphical user interface. An arrangement of the first, second, and third plurality of image vignettes in the graphical user interface can depend on a size and/or orientation of the display of the client device executing the client application. In some embodiments, a specified function in the graphical user interface can be disabled in response to determining a size of the display of the client device that fails to satisfy a threshold size. As an example, the system 100 can disable a function that allows the user to view a composite image corresponding to an image vignette that is rendered in the graphical user interface and/or can disable a function for rendering more image vignettes in the graphical user interface if it is determined that the size of the display does not satisfy a threshold size. As another example, the function that allows the user to use a magnifying glass function to hover over a portion of an image vignette to magnify that portion can be disable in the graphical user interface by the system 100 if it is determined that the size of the display does not satisfy the threshold size.

In some embodiments, at least one on-boarding question to the user is rendered in the graphical user interface, and the system determines which image vignettes to include in the first plurality of image vignettes rendered in the graphical user interface based on an answer received from the user to the at least one on-boarding question.

Figure 13:
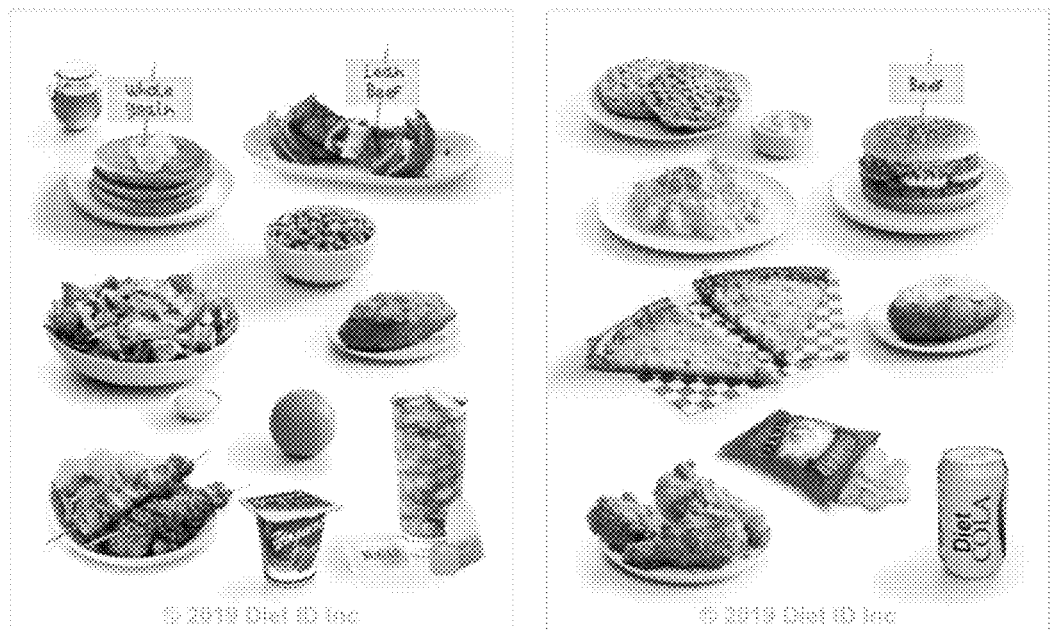
FIGS. 13-24 depict screen shots of a graphical user interface in accordance with embodiments of the present disclosure.
Figure 14:
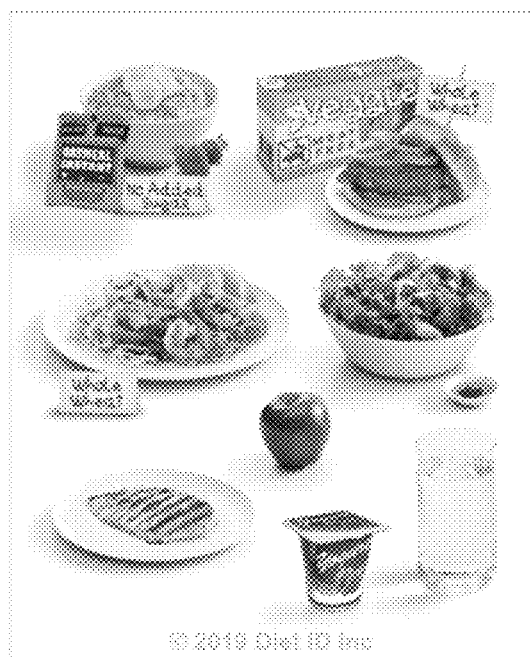
Figure 14:
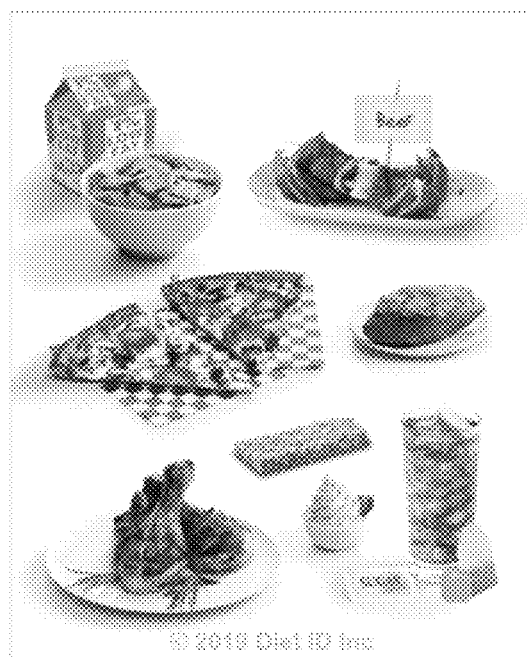
Figure 15:
Figure 16:
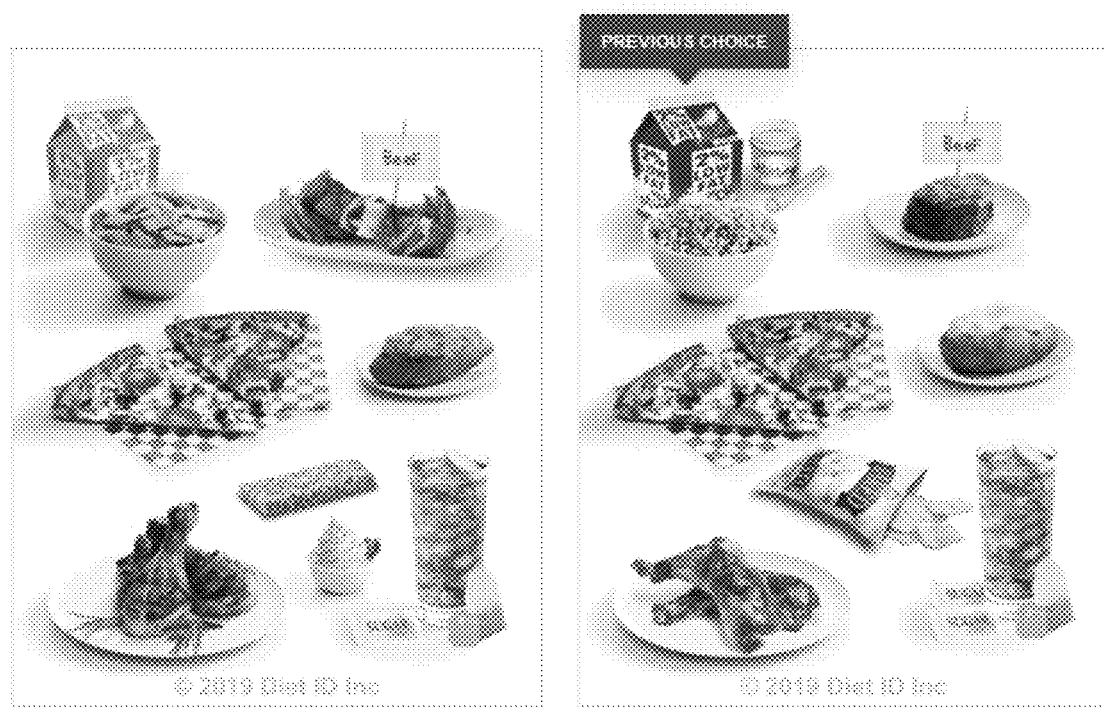
Figure 17:
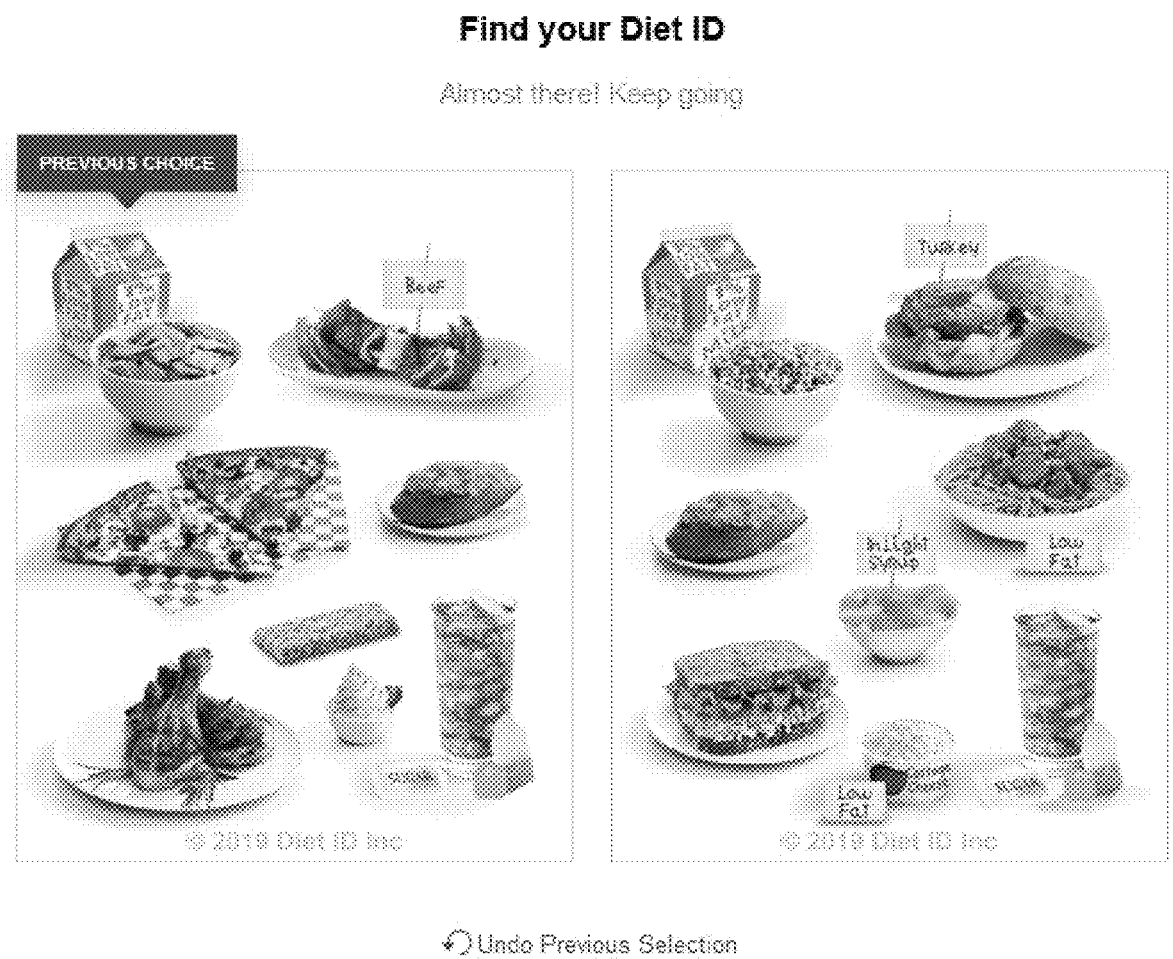
Figure 18:
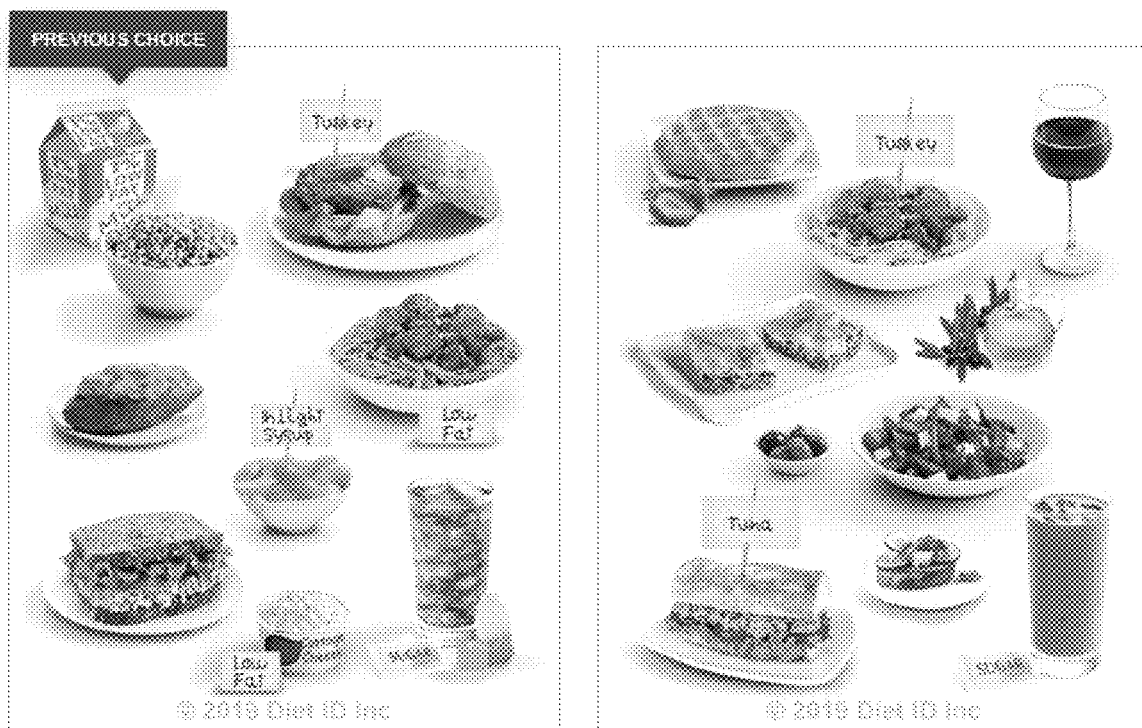
Figure 19:
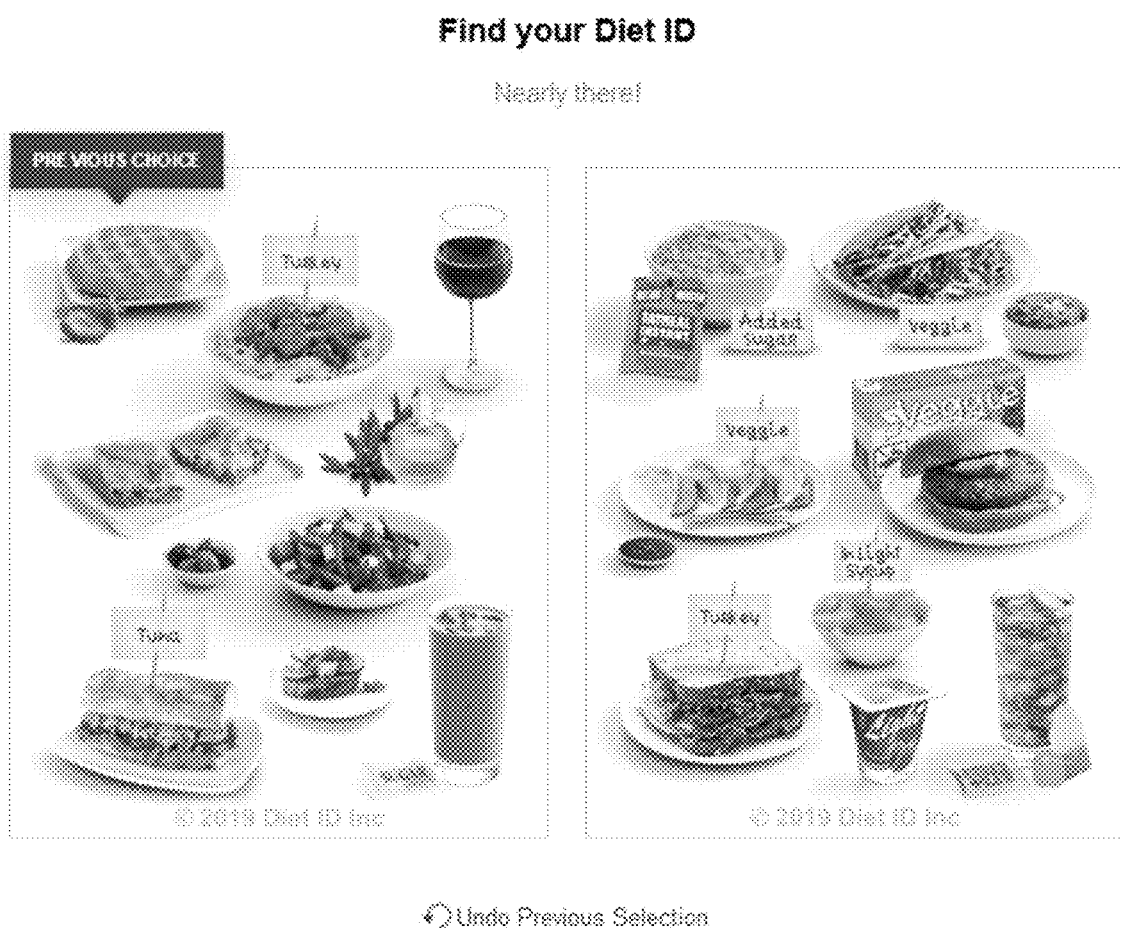
Figure 20:
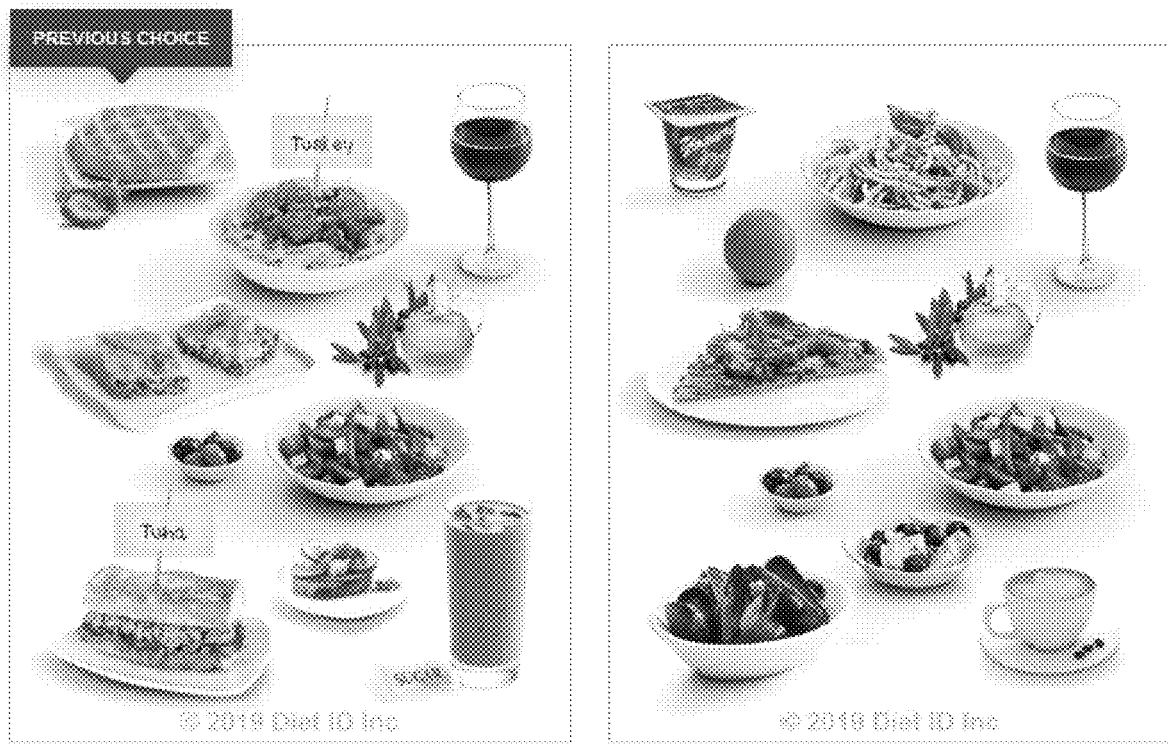
Figure 21:
Figure 22:
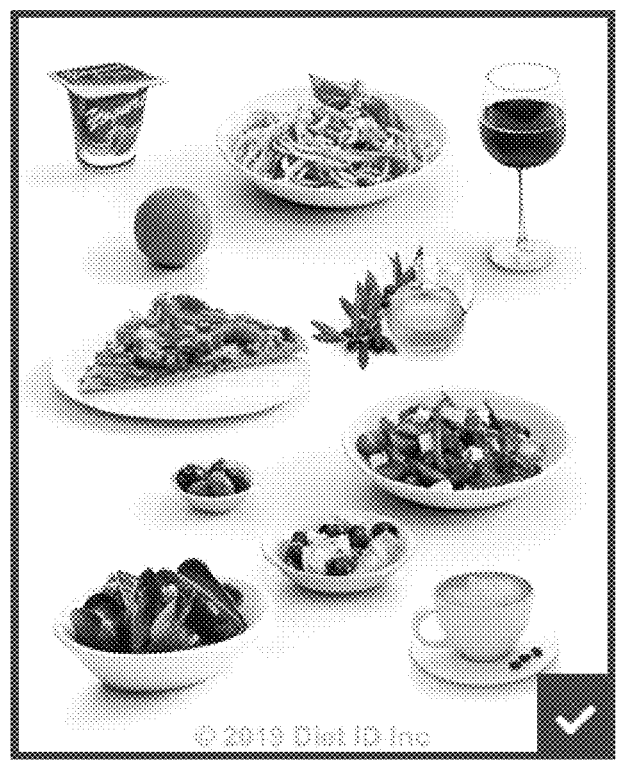

As depicted in FIG. 13, a user is presented with a graphical user interface displaying a scroll bar containing two unique derivative image vignettes and invited to select a derivative image vignette from the displayed derivative image vignettes that better represents the foods the user typically eats. Upon selection of an image (in this Example, the user selected the image on the left), the user is again presented with two unique image vignettes as shown in FIG. 14, each of which is different from the image vignettes displayed in FIG. 13 and invited to choose again. This step is repeated several times as shown in FIGS. 15, 16, and 17. As noted in FIGS. 16 and 17, one of the image vignettes displayed is the same as on the previous selection screen, indicating that the displayed images as selected by the user more closely approximate foods that they typically eat. This is further shown in FIGS. 18-21 as the processor continues to evaluate the image vignette selected by the user on each screen and display another set of image vignettes to home in on the user's diet. This completed process is shown in FIG. 22 which depict the identified diet based on the user's input. In this instance, the graphical user interface displays the typical diet of the user as a Quality 7 Mediterranean diet. By selecting the "i:" in the image shown in FIG. 22, the user is shown the elements that make up a "Quality 7 Mediterranean" diet, as shown in FIG. 23.

Figure 23:
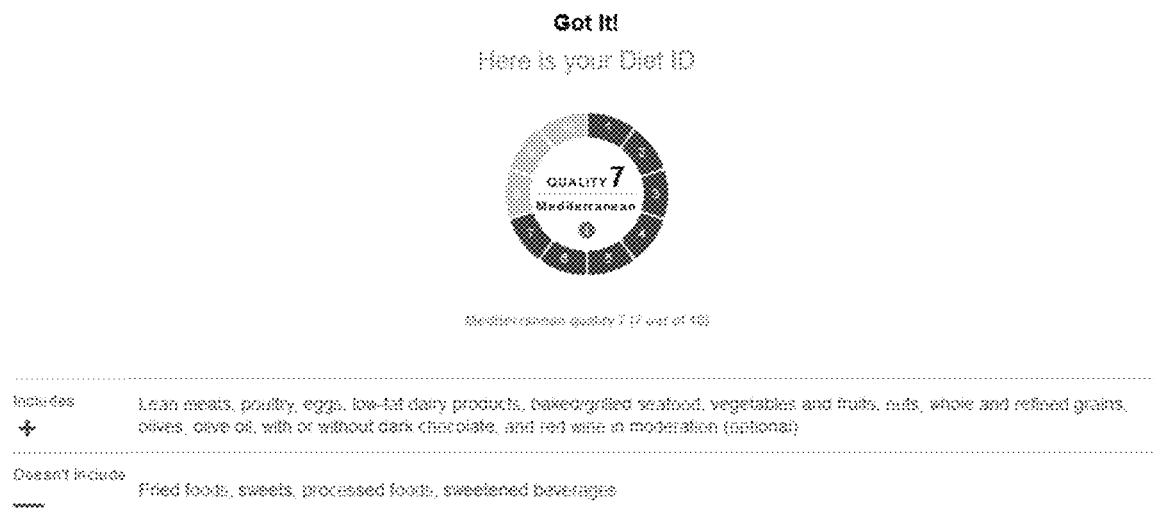
Figure 24:
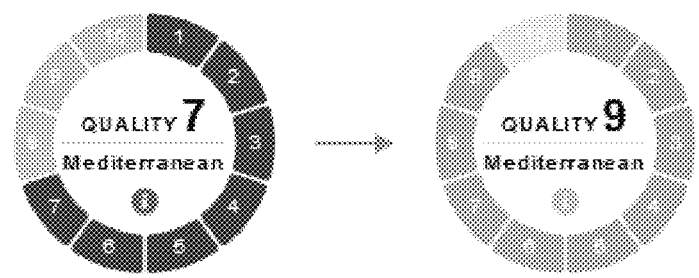
Figure 24:
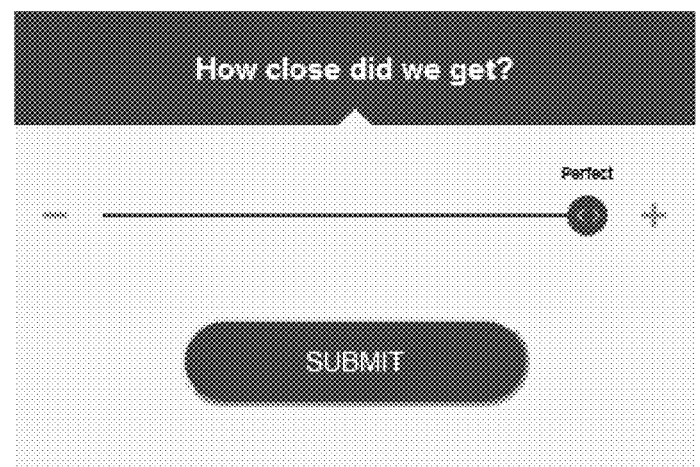

Thereafter, the user is presented with another scroll bar on the graphical user interface and invited to identify any goals (i.e., gain weight, lose weight, decrease inflammation, decrease blood pressure, etc.) and any diet customization and the processor calculates a personalized route to reach a "Diet Ideal" as depicted in FIG. 23. As shown in FIG. 24, the graphical user interface displays recommendations to the user to increase/decrease certain foods in their diet to reach their "Diet Ideal."

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than the order shown in the illustrative flowcharts.

The foregoing description of the specific embodiments of the subject matter disclosed herein has been presented for purposes of illustration and description and is not intended to limit the scope of the subject matter set forth herein. It is fully contemplated that other various embodiments, modifications and applications will become apparent to those of ordinary skill in the art from the foregoing description and accompanying drawings. Thus, such other embodiments, modifications, and applications are intended to fall within the scope of the following appended claims. Further, those of ordinary skill in the art will appreciate that the embodiments, modifications, and applications that have been described herein are in the context of particular environment, and the subject matter set forth herein is not limited thereto, but can be beneficially applied in any number of other manners, environments and purposes. Accordingly, the claims set forth below should be construed in view of the full breadth and spirit of the novel features and techniques as disclosed herein.

What is claimed is:

1. A method for an image-based dietary assessment system, the method comprising:
   receiving, at a server, a request for a sequence of images from a client device;
   querying, via the server, a database including a plurality of records including seed images and attributes associated with content depicted in the seed images to retrieve a set of seed image files based on information included in the request, the content including a least one of food or beverages,
   wherein the seed images are composite images or elemental images each associated with a multi-day dietary intake pattern;
   iteratively eliminating the seed image files in the set of seed image files by the server, based on the attributes stored in the database for the seed images, to define a selected subset of seed images, the subset containing fewer images than in the set of seed image files;
   extracting, via the server, elements from the seed images in the subset of seed images;
   generating one or more image vignettes, each image vignette incorporating at least two of the elements extracted from the seed images in the subset of seed images,
   wherein each of the one or more image vignettes presents dietary characteristics of at least one of a different diet quality level or a different diet type and is associated with the multi-day dietary intake pattern; and
   exporting, via the server, the one or more image vignettes to the client device as the sequence of images,
   wherein a quantity of image vignettes the server generates and exports depends at least in part on a property associated with the client device.

2. The method of claim 1, wherein the property of the client device is at least one of a size of a display of the client device, an available memory capacity of the client device, or a network connection speed at which the client device is operating.

3. The method of claim 1, further comprising:
allocating a temporary memory location for storing the one or more image vignettes;
storing instances of the one or more image vignettes in the temporary memory; and deleting, by the server, the instances of the one or more image vignettes from the temporary after the one or more image vignettes are exported to deallocate the temporary memory location.

4. The method of claim 1, wherein each seed image is assigned a diet type and a diet quality level based on the attributes associated with the content of the seed images.

5. The method of claim 1, wherein the one or more seed images are at least one of a composite image depicting a unique inventory of proportions of foods, ingredients, dishes and meals representative of a diet quality level X of a diet type N for a period of time or an elemental image of an integrated unit of food or a beverage.

6. The method of claim 1, wherein iteratively eliminating the seed image files in the set of seed image files to define the selected subset of seed images comprises:
determining which of the seed image files in the set of seed image files satisfy a specified diet type based on attributes associate with the specified diet type and attributes associated with the seed images;
eliminating the seed image files in the set that fail to satisfy the specified diet type from the set of seed image files
determining which of seed image files remaining in the set of seed image files satisfy a threshold diet quality based on attributes associate with the specified diet quality and attributes associated with the seed images; and
eliminating the seed image files in the set that fail to satisfy the threshold diet quality.

7. The method of claim 6, wherein iteratively eliminating the seed image files in the set of seed image files to define the selected subset of seed images further comprises:
determining which of the seed image files remaining in the set of seed image files include prevalent elements associated with a specified diet type, prevalent elements being elements that exceed a presence threshold in the specified diet type;
eliminating the seed image files in the set that are devoid of prevalent elements associated with the specified diet quality;
determining which of the seed image files remaining in the set of seed image files include elements consumed at a rate greater than a frequency threshold for the specified diet type;
eliminating seed image files in the set that do not satisfy the specified frequency threshold;
determining which of the seed image files remaining in the set of seed image files include elements that proportionally contribute to the specified diet type by greater than a threshold proportion for the specified diet type;
eliminating seed images files in the set that fail to satisfy the threshold proportion;
determining which of the seed image files remaining in the set of seed image files include elements that are representative of the specified diet type;
eliminating seed images files in the set of seed image files that are determined not to be representative of the specified diet type;
determining which of the seed image files remaining in the set of seed image files include elements that differentiate the specified diet type from other diet types;
eliminating seed images files in the set that fail to satisfy a specified exclusivity threshold;
determining which of the seed image files remaining in the set of seed image files include elements that have already been included in a threshold number of other image vignettes;
eliminating seed images files in the set of seed image files that have been included in the threshold number of other image vignettes;
determining which of the seed image files remaining in the set of seed image files include elements that can be alternatively inserted in the one or more image vignettes; and
selecting the seed image files remaining in the set of seed image files that satisfy a minimum criteria for the one or more image vignettes as the subset of seed image files.

8. A method for an image-based dietary assessment system, the method comprising:
a first database including a plurality of records including elemental images and attributes associated with content depicted in the elemental images, the content including a least one of a food or a beverage, the attributes defining one or more of a type of multi-day diet pattern and a quality of a multi-day diet pattern;
querying, via a server, the first database to retrieve a set of elemental image files for a specified type of multi-day diet pattern;
iteratively eliminating the elemental image files in the set of elemental image files by the server, based on the attributes stored in the database for the elemental images, to define a selected subset of elemental image files, the subset containing fewer images than in the set of elemental image files;
extracting, via the server, elements from the elemental images in the subset of elemental image files;
creating a new image file defining an image canvas;
inserting the elements extracted from the elemental images into the image canvas at specified locations to generate an image vignette associated with the multi-day diet pattern, the image vignette incorporating at least two of the elements extracted from the elemental images in the subset of elemental images
wherein the image vignette presents dietary characteristics of at least one of a different diet quality level or a different diet type and is associated with a-specific multi-day diet pattern;
storing the new image file; and
creating a record in a second database for the image vignette and associating the record with a diet type and diet quality level.

9. The method of claim 8, wherein iteratively eliminating the elemental image files in the set of elemental image files to define the selected subset of elemental images comprises:
determining which of the elemental image files in the set of elemental image files satisfy a specified diet type based on attributes associate with the specified diet type and attributes associated with the elemental images; and eliminating the elemental image files in the set that fail to satisfy the specified diet type from the set of elemental image files.

10. The method of claim 8, wherein iteratively eliminating the elemental image files in the set of elemental image files to define the selected subset of elemental images further comprises:
   determining which of elemental image files remaining in the set of elemental image files satisfy a threshold diet quality based on attributes associate with the specified diet quality and attributes associated with the elemental images; and
   eliminating the elemental image files in the set that fail to satisfy the threshold diet quality.

11. The method of claim 10, wherein iteratively eliminating the elemental image files in the set of elemental image files to define the selected subset of elemental images further comprises:
   determining which of the elemental image files remaining in the set of elemental image files include prevalent elements associated with a specified diet type; and
   eliminating the elemental image files in the set that are devoid of prevalent elements associated with the specified diet quality from the set of elemental image files.

12. The method of claim 11, wherein iteratively eliminating the elemental image files in the set of elemental image files to define the selected subset of elemental images further comprises:
   determining which of the elemental image files remaining in the retrieved set of elemental image files include elements consumed at a rate greater than a frequency threshold for the specified diet type; and
   eliminating elemental image files in the set that do not satisfy the specified frequency threshold.

13. The method of claim 12, wherein iteratively eliminating the elemental image files in the set of elemental image files to define the selected subset of elemental images further comprises:
   determining which of the elemental image files remaining in the set of elemental image files include elements that proportional contribute to the specified diet type by greater than a threshold proportion for the specified diet type; and
   eliminating elemental images files in the set that fail to satisfy the threshold proportion.

14. The method of claim 13, wherein iteratively eliminating the elemental image files in the set of elemental image files to define the selected subset of elemental images further comprises:
   determining which of the elemental image files remaining in the set of elemental image files include elements that are representative of the specified diet type;
   eliminating elemental images files in the set of elemental image files that are determine not to be representative of the specified diet type;
   determining which of the elemental image files remaining in the set of elemental image files include elements that differentiate the specified diet type from other diet types;
   eliminating elemental images files in the set that fail to satisfy a specified exclusivity threshold;
   determining which of the elemental image files remaining in the set of elemental image files include elements that have already been included in a threshold number of other image vignettes;
   eliminating elemental images files in the set of elemental image files that have been included in a threshold number of other image vignettes;
   determining which of the elemental image files remaining in the set of elemental image files include elements that can be alternatively inserted in the image vignette; and
   selecting the elemental image files remaining in the set of elemental image files that satisfy a minimum criteria for the image vignette as the subset of elemental image files.

15. A method for an image-based dietary assessment system, the method comprising:
   generating image vignettes for each of a plurality of diet type and diet quality combinations from a previously stored set of images of at least one of food and beverages, the image vignettes each including a subset of a total amount of elements from the set of images and associated with a multi-day dietary intake pattern, the subset containing fewer elements than in the set of images;
   iteratively rendering a first plurality of image vignettes in a graphical user interface for selection by a user, wherein each of the image vignettes in the first plurality of image vignettes presents dietary characteristics of at least one of a different diet quality level or a different diet type;
   receiving one or more first selections from the user in the graphical user interface of one or more of the image vignettes of the first plurality of the image vignettes;
   in response to receiving the one or more first selections in the graphical user interface, iteratively rendering a second plurality of image vignettes in the graphical user interface for selection by the user, the second plurality of image vignettes being selected based on the first selection by the user and includes at least one image vignette that is different from the image vignettes in the first plurality of image vignettes;
   receiving one or more second selections from the user in the graphical user interface of one or more of the image vignettes of the second plurality of image vignettes;
   in response to receiving the one or more second selections in the graphical user interface, iteratively rendering a third plurality of image vignettes in the graphical user interface for selection by the user, wherein at least one of the image vignettes in the third plurality of image vignettes is different from the second plurality of images vignettes;
   receiving one or more third selections from the user in the graphical user interface of one or more of the image vignettes in the third plurality of image vignettes;
   determining a user specific assessment of diet quality and type and an estimate of caloric intake and nutritional data for the user based on the one or more first, one or more second, and one or more third selections, wherein the one or more first selections are used to determine a diet type of the user and the one or more second selections and the one or more third selections are used to determine a diet quality level of the user; and
   rendering the user specific assessment of diet quality and type and the estimate of caloric intake and nutritional data in the graphical user interface,
   wherein an arrangement of the first, second, and third plurality of image vignettes depends on a size or orientation of the display of the client device executing the client application.

16. The method of claim 15, wherein each image vignette is derived from a composite image and depicts a unique inventory of proportions of foods, ingredients, dishes and meals representative of a specified diet quality level of a specified diet type for a period of time, and wherein the user can access the composite image associated with the derived image vignette.

17. The method of claim 15, wherein additional pluralities of image vignettes are rendered for selection as part of a repetitive processes until a type of diet and a level of diet quality is capable of being calculated for the user.

18. The method of claim 15, further comprising disabling a specified function in the graphical user interface in response to determining a size of the display of the client device that fails to satisfy a threshold size.

19. The method of claim 15, wherein prior to rendering the first plurality of image vignettes in the graphical user interface, at least one on-boarding question to the user is rendered in the graphical user interface, and the method further comprises:

determining which image vignettes to include in the first plurality of image vignettes rendered in the graphical user interface based on an answer received from the user to the at least one on-boarding question.

\* \* \* \* \*